US00RE49076E

(19) United States
(12) Reissued Patent
Friedman et al.

(10) Patent Number: US RE49,076 E
(45) Date of Reissued Patent: May 17, 2022

(54) COMPOSITIONS AND METHODS FOR TREATING RENAL DISEASE

(71) Applicant: Beth Israel Deaconess Medical Center, Inc., Boston, MA (US)

(72) Inventors: David J. Friedman, Boston, MA (US); Martin R. Pollak, Boston, MA (US)

(73) Assignee: Beth Israel Deaconess Medical Center, Inc., Boston, MA (US)

(21) Appl. No.: 16/519,648

(22) Filed: Jul. 23, 2019

Related U.S. Patent Documents

Reissue of:
(64) Patent No.: 9,023,355
Issued: May 5, 2015
Appl. No.: 13/404,725
Filed: Feb. 24, 2012

U.S. Applications:
(60) Division of application No. 15/896,744, filed on Feb. 14, 2018, now abandoned, which is a division of application No. 15/588,382, filed on May 5, 2017, now abandoned, which is an application for the reissue of Pat. No. 9,023,355, which is a continuation-in-part of application No. PCT/US2011/032924, filed on Apr. 18, 2011.

(60) Provisional application No. 61/489,140, filed on May 23, 2011, provisional application No. 61/325,343, filed on Apr. 18, 2010.

(51) Int. Cl.

| | |
|---|---|
| ***A61K 39/395*** | (2006.01) |
| ***G01N 33/92*** | (2006.01) |
| ***G01N 33/68*** | (2006.01) |
| ***C12Q 1/68*** | (2018.01) |
| ***C07K 16/18*** | (2006.01) |
| ***C12Q 1/6883*** | (2018.01) |

(52) U.S. Cl.
CPC ..... *G01N 33/92* (2013.01); *C07K 16/18* (2013.01); *C12Q 1/6883* (2013.01); *G01N 33/6893* (2013.01); *C12Q 2600/156* (2013.01); *G01N 2333/16* (2013.01); *G01N 2800/347* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 7,585,511 | B2 | 9/2009 | Pays et al. |
| 7,747,392 | B2 | 6/2010 | Ruano et al. |
| 10,927,377 | B2 | 2/2021 | Freier |
| 2005/0009016 | A1 | 1/2005 | Moskowitz et al. |
| 2005/0142596 | A1 | 6/2005 | Krolewski et al. |
| 2009/0075254 | A1 | 3/2009 | Ruano et al. |
| 2009/0162333 | A1 | 6/2009 | Pays et al. |
| 2010/0120781 | A1 | 5/2010 | Neamati |
| 2010/0297660 | A1 | 11/2010 | Winkler et al. |
| 2012/0128682 | A1 | 5/2012 | Pays et al. |
| 2012/0195902 | A1 | 8/2012 | Friedman et al. |
| 2013/0079244 | A1 | 3/2013 | Genovese et al. |
| 2015/0297598 | A1 | 10/2015 | Friedman et al. |

FOREIGN PATENT DOCUMENTS

| | | | | |
|---|---|---|---|---|
| WO | WO-2004/012757 | A2 | 2/2004 | |
| WO | WO-2004/012757 | A2 | 2/2004 | |
| WO | WO-2011/020865 | A1 | 2/2011 | |
| WO | WO-2011/071935 | A2 | 6/2011 | |
| WO | WO-2011/133474 | A2 | 10/2011 | |
| WO | WO-2011133474 | A2 * | 10/2011 | ..... C12Q 1/6883 |
| WO | WO-2012/162394 | A2 | 11/2012 | |

OTHER PUBLICATIONS

Genovese et al (Science 2010, vol. 329, pp. 841-845) (Year: 2010).*
Freidman (Clinical Journal of the American Society of Nephrology, 2021, vol. 16, pp. 294-303) (Year: 2021).*
Xu et al. (Asian Journal of Pharmaceutical Sciences, 2015, vol. 10, pp. 1-12) (Year: 2015).*
International Search Report and Written Opinion of the International Searching Authority for International Application No. PCT/US12/39145, dated Dec. 7, 2012 (14 pages).
Kaufman et al., "Transgenic analysis of a 100-kb human beta-globin cluster-containing DNA fragment propagated as a bacterial artificial chromosome," Blood. 94(9):3178-84 (1999).
Lecordier et al., "C-terminal mutants of apolipoprotein L-l efficiently kill both *Trypanosoma brucei brucei* and *Trypanosoma brucei rhodesiense,"* PLoS Pathog. 5(12):e1000685 (2009) (11 pages).
Paul, "Genes linked to kidney disease," Genetics Abstracts, <http://geneticabstracts.blogspot.com/2008/10/genes-linked-to-kidney-disease.html>, retrieved on Aug. 22, 2011 (2 pages).
NCBI Reference SNP(refSNP) Cluster Report: rs60910145, <http://www.ncbi.nlm.nih.gov/projects/SNP/snp_ref.cgi?rs=60910145>, retrieved on Dec. 15, 2011 (3 pages).
NCBI Reference SNP(refSNP) Cluster Report: rs73885319, <http://www.ncbi.nlm.nih.gov/projects/SNP/snp_ref.cgi?rs=73885319>, retrieved Dec. 15, 2011 (3 pages).
Vanhollebeke et al., "Human Trypanosoma evansi infection linked to a lack of apolipoprotein L-I," N Engl J Med. 355(26):2752-6 (2006).

(Continued)

*Primary Examiner* — Bruce R Campell
(74) *Attorney, Agent, or Firm* — Clark & Elbing LLP

(57) ABSTRACT

Compositions and methods are disclosed herein for treating or reducing the symptoms of a renal disease, such as focal segmental glomerulosclerosis (FSGS), hypertensive end-stage kidney disease (ESKD), and HIV-associated nephropathy (a distinct form of FSGS, also termed collapsing glomerulopathy). The compositions include the common variant of APOL1 and fragments thereof, as well as antibodies and fragments thereof that bind and neutralize pathogenic APOL1, nucleic acid molecules that encode the common variant of APOL1 and fragments thereof, and other compounds that bind and neutralize pathogenic APOL1. The methods of the invention include administering one or more of the compositions of the invention to a subject having or at risk of developing renal disease.

28 Claims, 1 Drawing Sheet

Specification includes a Sequence Listing.

(56) References Cited

OTHER PUBLICATIONS

Vanhollebeke et al., "Distinct roles of haptoglobin-related protein and apolipoprotein L-I in trypanolysis by human serum," Proc Natl Acad Sci USA. 104(10):4118-23 (2007).
Li et al., "Distribution and effect of apoL-I genotype on plasma lipid and apolipoprotein levels in Chinese normalipidemic and endogenous hypertriglyceridemic subjects," Clin Chim Acta. 403(1-2):152-5 (2009).
Freedman et al., "The apolipoprotein L1 (APOL1) gene and nondiabetic nephropathy in African Americans," J Am Soc Nephrol. 21 (9):1422-6 (2010) (5 pages).
International Search Report for International Application No. PCT/US11/32924, dated Apr. 9, 2012 (6 pages).
Written Opinion of the International Searching Authority for International Application No. PCT/US11/32924, dated Apr. 9, 2012 (8 pages).
Kiberstis. "Letter and reviews from Science (1189125)". E-mail to Martin Pollak. Mar. 16, 2010 (3 pages).
Velthuysen et al., "Glomerulopathy associated with parasitic infections" Clin Microbiol Rev. 13(1):55-66 (2000).
Nichols et al., "Innate immunity pathways regulate the nephropathy gene *Apoliprotein L1*," available in PMC Aug. 1, 2015, published in final edited form as: Kidney Int. 87(2): 332-342 (2015) (23 pages).
Aghajan et al., "Antisense oligonucleotide treatment ameliorates IFN-gamma-induced proteinuria in APOL1-transgenic mice," JCI Insight. 4(12):e126124 (2019) (20 pages).
Gibson et al., "The human serum resistance associated gene is ubiquitous and conserved in *Trypanosoma brucei rhodesiense* throughout East Africa," Infect Genet Evol 1(3):207-14 (2002).
Office Action in U.S. Appl. No. 13/404,725 dated Aug. 26, 2013 (11 pages).
Genovese et al. "Association of trypanolytic ApoL1 variants with kidney disease in African Americans," Science. 329(5993):841-5 (2010).
Juengst, "What next for human gene therapy? Gene transfer often has multiple and unpredictable effects on cells," BMJ 326(7404):1410-1 (2003).
Molina-Portela et al., "Distinct roles of apolipoprotein components within the trypanosome lytic factor complex revealed in a novel transgenic mouse model," J Exp Med. 205(8):1721-8 (2008).
Page et al., "Polymorphisms in the Apolipoprotein L1 gene and their effects on blood lipid and glucose levels in middle age males," Genes Nutr. 1(2):133-5 (2006).
Page et al., "The human apolipoprotein L gene cluster: identification, classification, and sites of distribution," Genomics 74(1):71-8 (2001).
Tzur et al. "Missense mutations in the APOL1 gene are highly associated with end stage kidney disease risk previously attributed to the MYH9 gene," Hum Genet. 128(3):345-50 (2010).
Van Hamme et al., "The trypanosome lytic factor of human serum and the molecular basis of sleeping sickness," Int J Parasitol 34(8):887-98 (2004).
Wang et al., "Rapid analysis of gene expression (RAGE) facilitates universal expression profiling," Nucelic Acids Res. 27(23):4609-18 (1999).

* cited by examiner

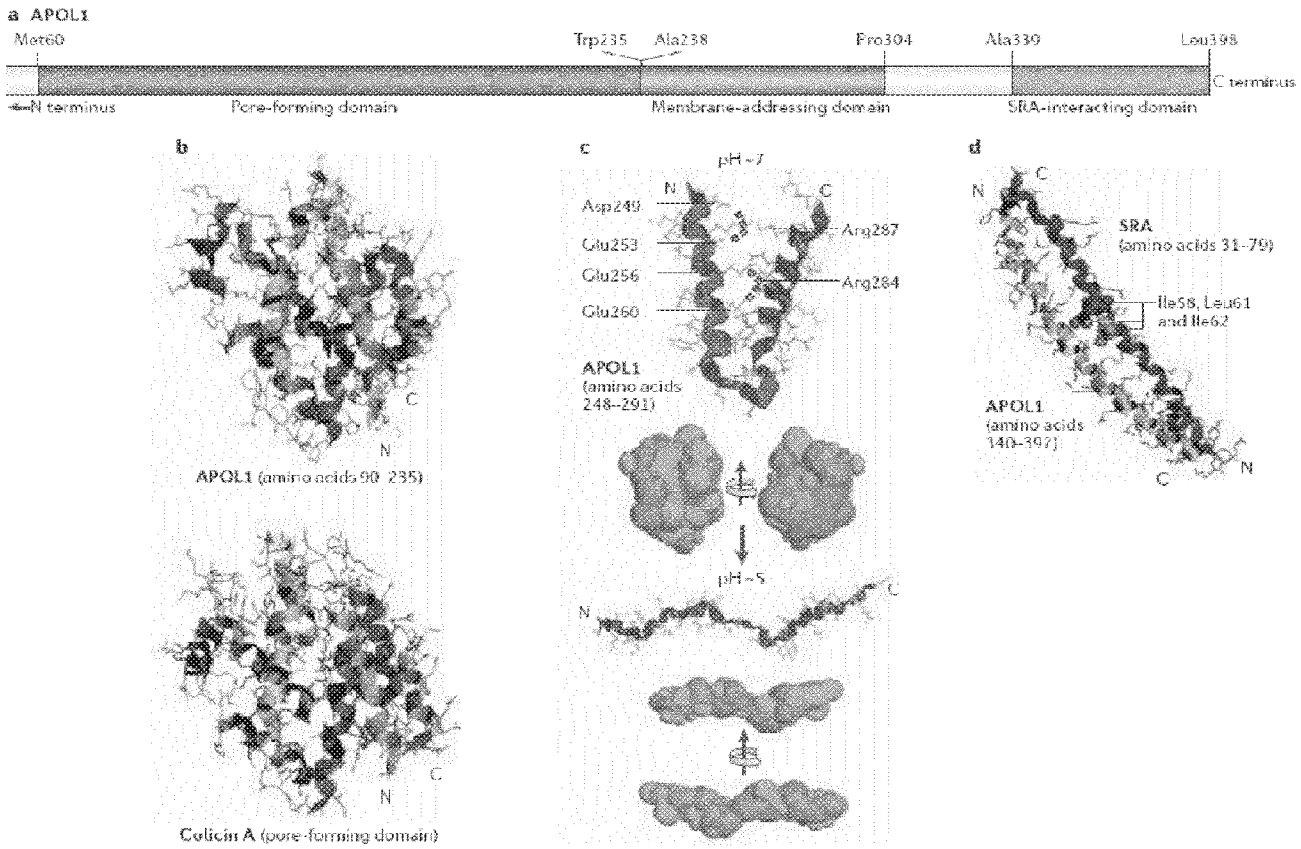
a APOL1
Met60
Trp235
Ala238
Pro304
Ala339
Leu398
N terminus
Pore-forming domain
Membrane-addressing domain
SRA-interacting domain
C terminus
b
APOL1 (amino acids 60–235)
Colicin A (pore-forming domain)
c
pH ~7
Asp249
Glu253
Glu256
Glu260
Arg287
Arg284
APOL1 (amino acids 248–291)
pH ~5
d
SRA (amino acids 31–79)
Ile58, Leu61 and Ile62
APOL1 (amino acids 140–397)

COMPOSITIONS AND METHODS FOR TREATING RENAL DISEASE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

*More than one reissue application has been filed for the reissue of U.S. Pat. No. 9,023,355.* This application *is a divisional reissue application of U.S. patent application Ser. No. 15/896,744, filed on Feb. 14, 2018, which is a divisional reissue application of U.S. patent application Ser. No. 15/588,382, filed on May 5, 2017, which is a reissue application of U.S. Pat. No. 9,023,355, granted May 5, 2015, which* claims priority to U.S. Provisional Patent Application No. 61/489,140, filed on May 23, 2011, and is a continuation-in-part application of International Application No. PCT/US2011/032924, filed on Apr. 18, 2011, which claims priority to U.S. Provisional Patent Application No. 61/325,343, filed on Apr. 18, 2010. [This application is also a continuation-in-part application of International Application No. PCT/EP2010/062065, filed on Aug. 18, 2010, which claims priority to U.S. Provisional Patent Application No. 61/323,727, filed on Apr. 13, 2010.] Each of these applications is incorporated by reference herein.

FIELD OF THE INVENTION

The invention features compositions and methods for treating renal disease, such as focal segmental glomerulosclerosis (FSGS), end-stage kidney disease (ESKD) or non-diabetic chronic kidney disease, in a subject (e.g., a subject having one or more APOL1 risk alleles). The compositions include the common variant of APOL1 and fragments thereof, as well as antibodies and fragments thereof that bind and neutralize APOL1, nucleic acid molecules that encode the common variant of APOL1 and fragments thereof, and other compounds that bind and neutralize APOL1. The methods of the invention include administering one or more of the compositions of the invention to a subject having or at risk of developing renal disease.

BACKGROUND OF THE INVENTION

End-stage kidney failure (ESKD) is a growing problem that now affects over half a million individuals in the United States. The cost of caring for patients with ESKD is currently over 40 billion dollars per year. In the U.S., the likelihood that subjects of African descent will develop ESKD is 4 to 5 times higher than for Americans without African ancestry. These facts are reflected in the disparity between the 12-13% of the U.S. population with African descent and the 40% of U.S. dialysis patients who are African-American. The epidemic of renal disease risk factors, such as obesity and metabolic syndrome, suggests that the magnitude of this problem will only increase.

There are no specific therapies for the vast majority of progressive kidney diseases. Some types of chronic renal disease progression can be slowed by blood pressure control with specific agents, but nephrologists cannot accurately predict which patients will respond. Moreover, while successful treatment typically slows progression, it neither prevents disease nor halts disease progression. We recently determined that the majority of non-diabetic kidney disease in African-Americans can be attributed to risk variants in the APOL1 gene. There still exists a need for therapies for kidney diseases that cause great morbidity and mortality with high economic impact in this and other subject populations.

SUMMARY OF THE INVENTION

Our invention uses APOL1 as the basis for the treatment of renal disease in a large population of renal disease patients whose disease is associated with the high-risk APOL1 genotype (e.g., those patients having at least one or more APOL1 risk alleles.

A first aspect of the invention features a method of treating or reducing the likelihood of development of a renal disease by administering to a subject in need thereof a composition that includes an agent that decreases a deleterious effect of a pathogenic APOL1. In several embodiments, the agent is:

i) a common APOL1 or fragment thereof;

ii) a nucleic acid molecule encoding a common APOL1 or fragment thereof;

iii) a ribonucleic acid interfering (RNAi) molecule that decreases the level of APOL1 polypeptide expression (e.g., a small interfering RNA (siRNA), a short hairpin RNA (shRNA), a double-stranded RNA (dsRNA), or a microRNA (miRNA)), in which preferably the agent is a nucleic acid molecule that decreases the level of pathogenic APOL1 polypeptide expression, relative to the level of pathogenic APOL1 polypeptide expression in the absence of the agent, but does not substantially decrease the level of common APOL1 polypeptide expression;

iv) an anti-APOL1 antibody or fragment thereof (e.g., the anti-APOL1 antibody or fragment thereof specifically binds to, and preferably neutralizes, a human pathogenic APOL1 polypeptide, but does not specifically bind, or binds at a substantially greater dissociation constant, to a common APOL1 polypeptide, in which preferably the pathogenic APOL1 polypeptide includes a S342G substitution (G1), a I384M substitution (G2), and/or a deletion removing amino acids N388 and Y389 (del6) or in which the pathogenic APOL1 polypeptide is a chimeric APOL1 polypeptide (e.g., a chimeric APOL1 polypeptide that includes all or a portion of a human APOL4 polypeptide); and/or v) a polypeptide that binds to, and preferably neutralizes, the pathogenic APOL1 polypeptide but not a common APOL1 polypeptide (e.g., a serum resistance-associated (SRA) polypeptide having at least 80% sequence identity to SEQ ID NO: 3 (e.g., at least 95% sequence identity to SEQ ID NO: 3), in which preferably the SRA polypeptide does not substantially bind to, or binds at a substantially greater dissociation constant, to a common APOL1 polypeptide).

In other embodiments, the chimeric APOL1 polypeptide includes one or more amino acids encoded by a coding or non-coding region of an APOL1 gene or an APOL4 gene or the chimeric APOL1 polypeptide causes or increases the likelihood of developing the renal disease in the subject. In yet another embodiment, the anti-APOL1 antibody or fragment thereof specifically binds a human APOL1 polypeptide having a S342G and an I384M mutation. Preferably, the anti-APOL1 antibody or fragment thereof does not specifically bind, or binds at a substantially greater dissociation constant, to a common APOL1 polypeptide. In still other embodiment, the common APOL1 fragment includes a sequence having at least 80% sequence identity to amino acids 360-379 of SEQ ID NO:2, in which preferably the common APOL1 fragment includes amino acids 360-379 of SEQ ID NO:2, or the common APOL1 fragment includes a sequence having at least 80% sequence identity to amino acids 339-398 of SEQ ID NO:2, in which preferably the common APOL1 fragment includes amino acids 339-398 of SEQ ID NO:2. In other embodiments, the anti-APOL1 antibody or fragment thereof specifically binds to an epitope of a human APOL1 polypeptide within a region that includes amino acid acids 339 to 398. In another embodiment, the anti-APOL1 antibody or fragment thereof does not substantially bind to, or binds at a substantially greater dissociation constant, to a common APOL1 polypeptide. In yet another embodiment, the anti-APOL1 antibody or fragment thereof specifically binds to, and preferably neutralizes, a human pathogenic APOL1, but not a human common APOL1.

In still other embodiments, the nucleic acid molecule encodes a polypeptide that includes a sequence having at least 80% sequence identity to amino acids 360-379 of SEQ ID NO:2 (e.g., preferably the nucleic acid molecule encodes a polypeptide that includes amino acids 360-379 of SEQ ID NO:2, and/or in which preferably the nucleic acid molecule does not include a sequence corresponding to an APOL1 risk allele). In other embodiment, the nucleic acid molecule encodes a polypeptide that includes a sequence having at least 80% sequence identity to amino acids 339-398 of SEQ ID NO:2 (e.g., preferably the nucleic acid molecule encodes a polypeptide that includes a sequence having amino acids 339-398 of SEQ ID NO:2, and/or in which preferably the nucleic acid molecule does not include a sequence corresponding to an APOL1 risk allele). In an embodiment, the method includes delivering the nucleic acid molecule into a cell of the subject, in which the nucleic acid molecule reduces or substantially inhibits expression of the pathogenic APOL1 in the cell.

In still other embodiment, the RNAi molecule includes a sequence that is complementary to at least 15 contiguous nucleotides (e.g., 20-100 contiguous nucleotides, such as 25 contiguous nucleotides) set forth within nucleotides 1-1197 of SEQ ID NO: 1 (e.g., preferably the sequence is complementary to at least 50 contiguous nucleotides set forth within nucleotides 1-1197 of SEQ ID NO: 1, and/or wherein preferably the RNAi molecule includes a sequence corresponding to an APOL1 risk allele). In other embodiments, the RNAi molecule includes a sequence that is complementary to at least 15 contiguous nucleotides set forth within nucleotides 1014-1197 of SEQ ID NO: 1 (e.g., preferably the sequence is complementary to at least 50 contiguous nucleotides set forth within nucleotides 1014-1197 of SEQ ID NO: 1). In yet another embodiment, the RNAi molecule includes a sequence that is complementary to at least 15 contiguous nucleotides set forth within nucleotides 1-200 of SEQ ID NO: 1 (e.g., preferably the sequence is complementary to at least 50 contiguous nucleotides set forth within nucleotides 1-200 of SEQ ID NO: 1). In an embodiment, the method includes delivering the RNAi molecule into a cell of the subject, in which the nucleic acid molecule reduces or substantially inhibits expression of the pathogenic APOL1 in the cell.

In still other embodiments, the agent of the invention treats or substantially inhibits development of renal disease or treats or reduces one or more symptoms associated with renal disease. In other embodiment, the renal disease specifically leads to damage of the kidneys (e.g., the renal disease is selected focal segmental glomerulosclerosis (FSGS), end-stage kidney disease (ESKD), hypertensive ESKD, nephropathy secondary to systemic lupus erythematosus, diabetic nephropathy, hypertensive nephropathy, IgA nephropathy, nephritis, human immunodeficiency virus (HIV)-associated nephropathy, and xanthine oxidase deficiency).

In yet other embodiments, the method further includes, prior to administering the agent, determining the expression of at least one pathogenic APOL1 in the subject (e.g., the determining step includes assaying for at least one single nucleotide polymorphism (SNP) in an APOL1 gene, in which preferably the SNP is present in a carboxy-terminal exon of the APOL1 gene (e.g., the SNP corresponds to the G1, G2, and/or del6 mutation), or assaying for at least one inversion in an APOL1 gene, in which preferably the inversion is in a 5' region of the APOL1 gene (e.g., the inversion is the G3 mutation that includes replacement of the 5' region of the APOL1 gene with a 5' region of an APOL4 gene).

In another embodiment, the subject is heterozygous for at least one or more APOL1 risk alleles that encode the pathogenic APOL1 or the subject is homozygous for at least one or more APOL1 risk alleles that encode the pathogenic APOL1. In still other embodiment, the subject is of African (an African-American subject) or Hispanic ancestry. In yet other embodiment, the subject is a human.

The method may further include administering to the subject one or more additional therapeutics. For example, a subject may also be treated using a blood pressure medication, a steroid, and/or an immunosuppressive agent. Examples of therapeutics include blood pressure medications (e.g., a diuretic (e.g., chlorthalidone, chlorothiazide, furosemide, hydrochlorothiazide, indapamide, metolazone, amiloride hydrochloride, spironolactone, triamterene, bumetanide, or a combination thereof), an alpha adrenergic antagonist (e.g., alfuzosin, doxazosin, prazosin, terazosin, or tamsulosin, or a combination thereof), a central adrenergic inhibitor (e.g., clonidine, guanfacine, or methyldopa, or a combination thereof), an angiotensin converting enzyme (ACE) inhibitor (e.g., benazepril, captopril, enalapril, fosinopril, lisinopril, moexipril, perindopril, quinapril, ramipril, or trandolapril, or combinations thereof), an angiotensin II receptor blocker (e.g., candesartan, eprosartan, irbesartan, losartan, olmesartan, telmisartan, or valsartan, or combinations thereof), an alpha blocker (e.g., doxazosin, prazosin, or terazosin, or a combination thereof), a beta blocker (e.g., acebutolol, atenolol, betaxolol, bisoprolol, carteolol, metoprolol, nadolol, nebivolol, penbutolol, pindolol, propranolol, solotol, or timolol, or a combination thereof), a calcium channel blocker (e.g., amlodipine, bepridil, diltiazem, felodipine, isradipine, nicardipine, nifedipine, nisoldipine, or verapamil, or combination thereof), a vasodilator (e.g., hydralazine or minoxidil, or combination thereof), and a renin inhibitor (e.g., aliskiren), or combinations thereof), a steroid (e.g., a corticosteroid, such as cortisone, prednisone, methylprednisolone, or prednisolone), or an anabolic steroid (anatrofin, anaxvar, annadrol, bolasterone, decadiabolin, decadurabolin, dehydropiandrosterone (DHEA), delatestryl, dianiabol, dihydrolone, durabolin, dymethazine, enoltestovis, equipose, gamma hydroxybutyrate, maxibolin, methatriol, methyltestosterone, parabolin, primobolin, quinolone, therabolin, trophobolene, and winstrol), or an immunosuppressive agent, such as a glucocorticoid, a cytostatic, an antibody, or an anti-immunophilin and/or mychophenolate mofetil (MMF), FK-506, azathioprine, cyclophosphamide, methotrexate, dactinomycin, antithymocyte globulin (ATGAM), an anti-CD20-antibody, a muromonoab-CD3 antibody, basilizimab, daclizumab, cyclosporin, tacrolimus, voclosporin, sirolimus, an interferon, infliximab, etanercept, adalimumab, fingolimod, and/or myriocin).

A second aspect of the invention features the use of any one or more agents of the first aspect of the invention in a method of manufacturing a medicament for treating or reducing the likelihood of development of a renal disease in a subject in need thereof.

A third aspect of the invention features an isolated agent that decreases a deleterious effect of a pathogenic APOL1 in a subject. For example, the agent is selected from i) a fragment of a common APOL1; ii) a nucleic acid molecule encoding the common APOL1 fragment; iii) a nucleic acid molecule that decreases the level of APOL1 polypeptide expression (e.g., an antisense or RNAi molecule, such as a small interfering RNA (siRNA), a short hairpin RNA (shRNA), a double-stranded RNA (dsRNA), or a microRNA (miRNA); iv) an anti-APOL1 antibody or fragment thereof (e.g., an anti-APOL1 antibody or fragment thereof binds to, and preferably neutralizes a pathogenic APOL1); or v) an APOL1-binding polypeptide or fragment thereof that binds to, and preferably neutralizes, the pathogenic APOL1 but not a common APOL1; or vi) a nucleic acid molecule that encodes the APOL1-binding polypeptide or fragment thereof.

In another embodiment, the common APOL1 fragment includes a sequence having at least 80% sequence identity (e.g., 85%, 90%, 95%, or 99% or more sequence identity) to amino acids 360-379 of SEQ ID NO:2 (e.g., preferably the common APOL1 fragment includes amino acids 360-379 of SEQ ID NO:2). In still other embodiment, the common APOL1 fragment includes a sequence having at least 80% sequence identity (e.g., 85%, 90%, 95%, or 99% or more sequence identity) to amino acids 339-398 of SEQ ID NO:2 (e.g., preferably the common APOL1 fragment includes amino acids 339-398 of SEQ ID NO:2).

In still other embodiment, the nucleic acid molecule encodes a polypeptide that includes a sequence having at least 80% sequence identity (e.g., 85%, 90%, 95%, or 99% or more sequence identity) to amino acids 360-379 of SEQ ID NO:2 (e.g., preferably the nucleic acid molecule encodes a polypeptide that includes amino acids 360-379 of SEQ ID NO:2, and/or preferably the nucleic acid molecule does not include a sequence corresponding to an APOL1 risk allele). In other embodiments, the nucleic acid molecule encodes a polypeptide that includes a sequence having at least 80% sequence identity (e.g., 85%, 90%, 95%, or 99% or more sequence identity) to amino acids 339-398 of SEQ ID NO:2 (e.g., preferably the nucleic acid molecule encodes a polypeptide that includes a sequence having amino acids 339-398 of SEQ ID NO:2, and/or preferably the nucleic acid molecule does not include a sequence corresponding to an APOL1 risk allele.

In an embodiment, the anti-APOL1 antibody or fragment thereof specifically binds to, and preferably neutralizes, a human pathogenic APOL1 polypeptide, but does not specifically bind, or binds at a substantially greater dissociation constant, to a common APOL1 polypeptide (e.g., preferably the pathogenic APOL1 polypeptide includes a S342G substitution (G1), a I384M substitution (G2), and/or a deletion removing amino acids N388 and Y389 (del6), or preferably the pathogenic APOL1 polypeptide is a chimeric APOL1 polypeptide). In another embodiment, the anti-APOL1 antibody or fragment thereof specifically binds a human APOL1 polypeptide having a S342G and an I384M mutation (e.g., preferably the anti-APOL1 antibody or fragment thereof does not specifically bind, or binds at a substantially greater dissociation constant, to a common APOL1 polypeptide). In another embodiment, the anti-APOL1 antibody or fragment thereof specifically binds to an epitope of a human APOL1 polypeptide within a region that includes amino acid acids 339 to 398. In another embodiment, the anti-APOL1 antibody or fragment thereof does not substantially bind to, or binds at a substantially greater dissociation constant, to a common APOL1 polypeptide, or the anti-APOL1 antibody or fragment thereof specifically binds to, and preferably neutralizes, a human pathogenic APOL1, but not a human common APOL1.

In other embodiments, the chimeric APOL1 polypeptide includes all or a portion of a human APOL4 polypeptide or includes one or more amino acids encoded by a coding or non-coding region an APOL1 gene or an APOL4 gene. In still another embodiment, the chimeric APOL1 polypeptide causes or increases the likelihood of developing the renal disease in the subject.

In other embodiment, the nucleic acid molecule that decreases the level of APOL1 polypeptide expression (e.g., an RNAi molecule) includes a sequence that is complementary to at least 15 contiguous nucleotides set forth within nucleotides 1-1197 of SEQ ID NO: 1 (e.g., preferably the sequence is complementary to at least 50 contiguous nucleotides set forth within nucleotides 1-1197 of SEQ ID NO: 1, and/or in which preferably the nucleic acid molecule includes a sequence corresponding to an APOL1 risk allele. In other embodiments, nucleic acid molecule (e.g., an RNAi molecule) includes a sequence that is complementary to at least 15 contiguous nucleotides set forth within nucleotides 1014-1197 of SEQ ID NO: 1 (e.g., preferably the sequence is complementary to at least 50 contiguous nucleotides set forth within nucleotides 1014-1197 of SEQ ID NO: 1). In still other embodiment, the nucleic acid molecule (e.g., an RNAi molecule) includes a sequence that is complementary to at least 15 contiguous nucleotides set forth within nucleotides 1-200 of SEQ ID NO: 1 (e.g., preferably the sequence is complementary to at least 50 contiguous nucleotides set forth within nucleotides 1-200 of SEQ ID NO: 1).

In other embodiment, the agent is a serum resistance-associated (SRA) polypeptide having at least 80% sequence identity (e.g., 85%, 90%, 95%, or 99% or more sequence identity) to SEQ ID NO: 3 (e.g., the SRA polypeptide has at least 95% sequence identity to SEQ ID NO: 3) but does not have the sequence of SEQ ID NO:3. In yet another embodiment, the SRA polypeptide does not substantially bind to, or binds at a substantially greater dissociation constant, to a common APOL1 polypeptide.

In other embodiments, the agent is a nucleic acid molecule that is incorporated into a delivery vehicle.

A fourth aspect of the invention features a delivery vehicle that includes one or more of the nucleic acid molecules of the third aspect of the invention (e.g., a nucleic acid molecule that encodes an APOL1 polypeptide or fragment thereof or a nucleic acid molecule (e.g., an RNAi molecule) that decreases the level of expression of an APOL1 polypeptide).

A fifth aspect of the invention features a composition that includes one or more agents of the third aspect of the invention, and a pharmaceutically acceptable diluent or excipient, and/or a pharmaceutically acceptable salt thereof.

A sixth aspect of the invention features a method of treating or reducing the likelihood of development of a renal disease (e.g., focal segmental glomerulosclerosis (FSGS), end-stage kidney disease (ESKD), hypertensive ESKD, nephropathy secondary to systemic lupus erythematosus, diabetic nephropathy, hypertensive nephropathy, IgA nephropathy, nephritis, human immunodeficiency virus (HIV)- associated nephropathy, or xanthine oxidase deficiency) by extracorporeally contacting all or a portion of the blood or plasma from a subject with a composition that includes an agent that decreases a deleterious effect of a pathogenic APOL1 (e.g., one or more agents of the third aspect of the invention). In an embodiment, the contacting occurs during an apheresis procedure.

Definitions

By "apheresis," "hemapheresis," or "pheresis" is meant the process of removing a specific component from the blood, plasma, serum, or a fraction thereof, of a subject. Apheresis can be used to remove, separate, or collect one or more specific components of the blood, plasma, serum, or a fraction thereof. In general, apheresis includes the withdrawal of blood from the subject's body, removal of one or more components from the blood, and transfusion of the remaining blood back into the subject's body.

By "apolipoprotein L1" or "APOL1" is meant a gene encoding human apolipoprotein L, 1 (OMIM: 603743; see also SEQ ID NO: 1) or a polypeptide that includes, e.g., amino acids 1-398 of SEQ ID NO: 2. APOL1 is a secreted high density lipoprotein which binds to apolipoprotein A-I. Apolipoprotein A-I is a relatively abundant plasma protein and is the major apoprotein of HDL. Several different transcript variants encoding different isoforms have been found for this gene.

Nucleic acid and protein sequences for human APOL1 are publicly available. For example, GENBANK® Accession No. NC_000022.10 (nucleotides 36649117.36663577) discloses an exemplary human APOL1 genomic sequence (incorporated by reference as provided by GENBANK® on Apr. 18, 2010). In other examples, GENBANK® Accession Nos. AF305224.1, NM_003661.3, NM_145343.2, NM_001136540.1, z82215, and BC127186.1 disclose exemplary human APOL1 nucleic acid sequences, and GENBANK® Accession Nos. CAQ09089, NP_003652, AAI43039.1, and AAI42721.1 disclose exemplary human APOL1 protein sequences, all of which are incorporated by reference as provided by GENBANK® on Apr. 18, 2010.

By "APOL1 risk allele" is meant a form of a gene that is correlated with the development of, or an increased risk of developing, renal disease in a subject (e.g., a human). The risk allele may correspond to a mutation in an APOL1 gene (e.g., a human APOL1 gene) or a mutation in a gene that is involved in the expression of a protein that may interacts with an APOL1 protein or another component of the high density lipoprotein complex. The mutation may result in a modification (e.g., a substitution, deletion, or inversion) in a polypeptide product of a risk allele (e.g., a substitution, deletion, or inversion in an APOL1 polypeptide). Examples of such mutations in an APOL1 polypeptide include, but are not limited to, the G1, G2, del6, and G3 mutations described herein and in PCT/US2011/032924. The risk of renal disease is elevated in subjects carrying one or more (e.g., two, three, or four) APOL1 risk alleles.

By "common APOL1" is meant an APOL1 polypeptide, or nucleic acid molecule encoding the APOL1 polypeptide, having a sequence that is not correlated to the development of renal disease in a subject (e.g., a human). For example, a common APOL1 is one that includes an amino acid sequence or a nucleic acid sequence set forth above in the definition for "apolipoprotein L1" and "APOL1" (e.g., SEQ ID NOs: 1 and 2), and that does not include one or more mutations that have been correlated with the development of renal disease, such as the G1, G2, del6, and/or G3 mutations described herein and in PCT/US2011/032924.

By "decrease" is meant becoming less or smaller, as in number, amount, size, or intensity. In one example, decreasing the risk of a disease (such as FSGS or hypertensive ESKD) includes a decrease in the likelihood of developing the disease by at least about 20%, for example by at least about 30%, 40%, 50%, 60%, 70%, 80%, or 90%. In another example, decreasing the risk of a disease includes a delay in the development of the disease, for example a delay of at least about six months, such as about one year, such as about two years, about five years, or about ten years.

In one example, decreasing the signs and symptoms of renal disease (e.g., such as FSGS or hypertensive ESKD) includes decreasing the effects of the disease, such as podocyte injury or glomerular scarring by a desired amount, for example by at least 5%, at least 10%, at least 15%, at least 20%, at least 25%, at least 30%, at least 50%, at least 75%, or even at least 90%, as compared to a response in the absence of a therapeutic composition.

By "fragment" is meant a portion of a polypeptide (e.g., an APOL1 polypeptide, an anti-APOL1 antibody, or an APOL1 antagonist (e.g., an APOL1-binding polypeptide, such as an SRA) or nucleic acid molecule encoding an APOL1 polypeptide, an anti-APOL1 antibody, an APOL1 antagonist (e.g., an SRA), or an antisense APOL1 molecule) having a region that is substantially identical to a portion of a reference protein or nucleic acid and retains at least 50% or 75%, more preferably 80%, 90%, or 95%, or even 99% of at least one biological activity of the reference protein or nucleic acid, but does not include the entire amino acid or nucleic acid sequence of the full-length polypeptide or nucleic acid molecule. For example, the fragment may have at least 1, at least 5, at least 10, 20, 30, 40, 50, 60, 70 80, 90, or 100, or more (e.g., up to 200, 300 or more) fewer amino acid residues or nucleic acid bases relative to the full-length polypeptide or nucleic acid molecule (e.g., an APOL1 polypeptide, an anti-APOL1 antibody, or an APOL1 antagonist (e.g., an SRA) or nucleic acid molecule encoding an APOL1 polypeptide, an anti-APOL1 antibody, an APOL1 antagonist (e.g., an SRA), or an antisense APOL1 molecule). Thus, for example, an APOL1 polypeptide fragment of the invention may include a polypeptide having an amino acid sequence with fewer than 398 amino acids of SEQ ID NO: 2 (although the fragment may include other "non-APOL1" amino acid sequences and still be considered an APOL1 fragment).

By "isolated" (e.g., as an "isolated" biological component, such as a nucleic acid molecule, protein, antibody, or cell, or as an "isolated" chemical component, such as a compound or other chemical therapeutic agent) is meant that a component has been substantially separated or purified away from other biological (or chemical) components, e.g., as in the cell of an organism in which the component naturally occurs. For example, a component is "isolated" if it is enriched in a composition, relative to other components in the composition, such that it constitutes at least 30%, more preferably at least 50%, or even more preferably at least 75% or more of the composition. A component is "substantially isolated" or "substantially purified" if it is enriched, relative to other components in a composition, such that it constitutes at least 85%, more preferably at least 90%, or even more preferably 95%, 97%, or 99% or more of the composition. Nucleic acids and proteins that have been "isolated" include, e.g., nucleic acid molecules that encode an APOL1 polypeptide or fragment thereof and nucleic acid therapeutics of the invention, such an antisense APOL1 mRNA molecules, APOL1 polypeptides or fragments thereof and APOL1 antagonists, such as serum resistance-associated polypeptides or fragments thereof, and antibodies (e.g., anti-APOL1 antibodies or fragments thereof, each of which may be purified by standard purification methods. The term also embraces nucleic acid molecules and proteins prepared by recombinant expression in a host cell as well as chemically synthesized nucleic acid molecules, peptides, and polypeptides (e.g., one or more of the nucleic acid molecules, proteins, and antibodies of the invention).

By "pathogenic APOL1" is meant an APOL1 polypeptide, or nucleic acid molecule encoding the APOL1 polypeptide, having a sequence that is correlated to the development of renal disease in a subject (e.g., a human). For example, a pathogenic APOL1 is one that includes an amino acid sequence or a nucleic acid sequence set forth above in the definition for "apolipoprotein L1" and "APOL1" (e.g., SEQ ID NOs: 1 and 2), but that also includes one or more mutations that have been correlated with the development of renal disease, such as the G1, G2, del6, and/or G3 mutations described herein and in PCT/US2011/032924.

By "renal disease" is meant a disorder that specifically leads to damage of the kidneys. Renal diseases include but are not limited to FSGS, hypertensive ESKD, nephropathy secondary to systemic lupus erythematosus, diabetic nephropathy, hypertensive nephropathy, IgA nephropathy, nephritis, HIV-associated nephropathy, non-diabetic chronic kidney disease, and xanthine oxidase deficiency.

Renal disease can be chronic or acute. Chronic renal disease, or the type detected with the assays disclosed herein can progress from stage 1 to stage 2, stage 3, stage 4 or stage 5. The stages of chronic renal disease are:

Stage 1: Slightly diminished kidney function; Kidney damage with normal or increased GFR (>90 mL/min/1.73 m2). Kidney damage is defined as pathologic abnormalities or markers of damage, including abnormalities in blood or urine test or imaging studies.

Stage 2: Mild reduction in GFR (60-89 mL/min/1.73 m2) with kidney damage. Kidney damage is defined as pathologic abnormalities or markers of damage, including abnormalities in blood or urine test or imaging studies.

Stage 3: Moderate reduction in GFR (30-59 mL/min/1.73 m2)

Stage 4: Severe reduction in GFR (15-29 mL/min/1.73 m2)

Stage 5: Established kidney failure (GFR <15 mL/min/1.73 m2, or permanent renal replacement therapy (RRT)

By "sequence identity" or "sequence similarity" is meant that the identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

The NCBI Basic Local Alignment Search Tool (BLAST) (Altschul et al., J. Mol. Biol. 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: -i is set to a file containing the first nucleic acid sequence to be compared (such as C:\seq1.txt); -j is set to a file containing the second nucleic acid sequence to be compared (such as C:\seq2.txt); -p is set to blastn; -o is set to any desired file name (such as C:\output.txt); -q is set to −1; -r is set to 2; and all other options are left at their default setting. For example, the following command can be used to generate an output file containing a comparison between two sequences: C:\B12seq -i c:\seq1.txt -j c:\seq2.txt -p blastn -o c:\output.txt -q -1 -r 2.

To compare two amino acid sequences, the options of B12seq can be set as follows: -i is set to a file containing the first amino acid sequence to be compared (such as C:\seq1.txt); -j is set to a file containing the second amino acid sequence to be compared (such as C:\seq2.txt); -p is set to blastp; -o is set to any desired file name (such as C:\output.txt); and all other options are left at their default setting. For example, the following command can be used to generate an output file containing a comparison between two amino acid sequences: C:\B12seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (i.e., 1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

One indication that two nucleic acid molecules are closely related is that the two molecules hybridize to each other under stringent conditions that are well-recognized in the art. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least 60%, at least 70%, at least 80%, at least 90%, at least 95%, at least 98%, or at least 99% sequence identity (for example to a known APOL1 gene sequence (e.g., SEQ ID NO:1)) determined by the method described above. An alternative (and not necessarily cumulative) indication that two nucleic acid sequences are substantially identical is that the polypeptide which the first nucleic acid encodes is immunologically cross reactive with the polypeptide encoded by the second nucleic acid. One of skill in the art will appreciate that the particular sequence identity ranges are provided for guidance only. Similarly, identical or similar amino acids sequences can, for example, possess at least 60%, at least 70%, at least 80%, at least 90%, at least 95%, at least 98%, or at least 99% sequence identity (for example to a known APOL1 polypeptide sequence (e.g., SEQ ID NO: 2)) determined by the method described above.

By "specifically binds" is meant the preferential association of a binding moiety (e.g., an antibody, antibody fragment, or APOL1 antagonist) to a target molecule (e.g., a pathogenic APOL1) in a sample (e.g., a biological sample) or in vivo or ex vivo. It is recognized that a certain degree of non-specific interaction may occur between a binding moiety and a non-target molecule. Nevertheless, specific binding may be distinguished as mediated through specific recognition of the target molecule. Specific binding results in a stronger association between the binding moiety (e.g., an antibody or fragment thereof) and, e.g., an antigen (e.g., a pathogenic APOL1) than between the binding moiety and, e.g., a non-target molecule (e.g., a common APOL1). In one example, an antibody that specifically binds to an epitope in a pathogenic APOL1 that includes a mutation corresponding to an APOL1 risk allele does not specifically bind (or binds at a substantially lower affinity to) to the corresponding epitope in common APOL1 that lacks the mutation corresponding to the APOL1 risk allele. For example, the antibody may have, e.g., at least 10-fold greater affinity (e.g., 10, $10^2$-, $10^3$-, $10^4$-, $10^5$-, $10^6$-, $10^7$-, $10^8$-, $10^9$-, or $10^{10}$-fold greater affinity) to the pathogenic APOL1 isoform than to the common APOL1 isoform. For example, the antibody may specifically bind to an epitope of pathogenic APOL1 that includes a S342G substitution (G1), a I384M substitution (G2), a deletion removing amino acids N388 and Y389 (del6), and/or an inversion that produces a chimeric human APOL4/APOL1 polypeptide (e.g., an inversion in a 5' region of a human APOL1 gene in which the 5' region of an APOL1 gene is replaced with a 5' region of an APOL4 gene (G3)).

By "subject" or "patient" is meant a living multi-cellular vertebrate organism, a category that includes human and non-human mammals (such as laboratory or veterinary subjects).

By "therapeutically effective amount" is meant an amount of a therapeutic agent (e.g., an APOL1 polypeptide or fragment thereof, a nucleic acid molecule encoding an APOL1 polypeptide or fragment thereof, an anti-APOL1 antibody or fragment thereof, a nucleic acid molecule encoding an anti-APOL1 antibody or fragment thereof, an anti-APOL1 nucleic acid molecule, or an APOL1 protein antagonist of the invention (e.g., a SRA polypeptide)) that alone, or together with one or more additional (optional) therapeutic agents, induces a desired response. In one example, the desired response is decreasing the risk of developing FSGS or decreasing the signs and symptoms of FSGS. For example, a therapeutically effective amount of a human APOL1 polypeptide or fragment thereof, a nucleic acid molecule encoding a human APOL1 polypeptide or fragment thereof, an anti-APOL1 antibody or fragment thereof (e.g., an antibody that specifically binds to (and neutralizes) a human APOL1 polypeptide, such as an APOL1 polypeptide comprising a S342G substitution (G1), a I384M substitution (G2), a deletion removing amino acids N388 and Y389 (del6), and/or an inversion that produces a chimeric human APOL4/APOL1 polypeptide (e.g., an inversion in a 5' region of a human APOL1 gene in which the 5' region of an APOL1 gene is replaced with a 5' region of an APOL4 gene (G3))), a nucleic acid molecule encoding an anti-APOL1 antibody or fragment thereof, an anti-APOL1 nucleic acid molecule (e.g., an siRNA molecule that reduces expression of a human APOL1 polypeptide), or a human APOL1 protein antagonist (e.g., an SRA polypeptide that specifically binds pathogenic APOL1 but does not specifically bind (or binds at a substantially lower affinity to) common APOL1)) can be used to treat renal disease or reduce one or more symptoms associated with renal disease.

Ideally, a therapeutically effective amount provides a therapeutic effect without causing a substantial cytotoxic effect in the subject. The preparations disclosed herein are administered in therapeutically effective amounts. In general, a therapeutically effective amount of a composition administered to a subject (e.g., a human subject) will vary depending upon a number of factors associated with that subject, for example the overall health of the subject, the condition to be treated, or the severity of the condition. A therapeutically effective amount of a composition can be determined by varying the dosage of the product and measuring the resulting therapeutic response. The therapeutically effective amount can be dependent on the source applied, the subject being treated, the severity and type of the condition being treated, and the manner of administration.

In one example, a desired response is to prevent the development of renal disease (e.g., FSGS). In another example, a desired response is to delay the development or progression of renal disease (e.g., FSGS), for example, by at least about three months, at least about six months, at least about one year, at least about two years, at least about five years, or at least about ten years. In another example, a desired response is to decrease the signs and symptoms of renal disease (e.g., FSGS), such as inflammation and/or scarring of the tissues of the kidney, and/or neurological symptoms in the limbs or associated with speaking.

By "treatment," with respect to renal disease, is meant (1) inhibiting development of symptoms of the disease, e.g., causing the clinical symptoms of the disease not to develop in an animal (e.g., a human) that may have or be predisposed to develop the disease but does not yet experience or display symptoms of the disease, (2) inhibiting the disease, e.g., arresting the development of the disease or one or more of its clinical symptoms, or (3) relieving or ameliorating the disease, e.g., causing regression of the disease or one or more of its clinical symptoms. For example, treatment can refer to relieving one or more symptoms associated with renal disease. Treatment of a disease does not require a total absence of disease. For example, a decrease of at least 25% or at least 50% of one or more of the symptoms or undesired consequences of the disease can be sufficient.

BRIEF DESCRIPTION OF THE DRAWINGS

FIG. 1 is a schematic showing the structure of APOL1.

DETAILED DESCRIPTION

We recently discovered and reported genetic evidence demonstrating that the 4 to 5-fold increased risk of non-diabetic end-stage renal disease among African-Americans is caused primarily by mutations in the gene encoding Apolipoprotein L1 (APOL1), a component of the densest. HDL3 fraction of high-density lipoprotein. These mutations result in amino acid deletions, substitutions, and inversions (see, e.g., PCT/US2011/032924, which is incorporated herein by reference). APOL1 variants, commonly found among the subjects of African descent (e.g., African-Americans and subjects from some regions of Africa), are among the most powerful genetic risk factors for any disease yet described in terms of frequency and effect size. APOL1 variants can be identified by the presence of single nucleotide polymorphisms (SNPs) in the APOL1 gene (e.g., a SNP within the C-terminal exon of an APOL1 gene, such as the G1 and/or G2 risk alleles), a deletion in the APOL1 gene (e.g., del6), and/or at least one inversion in an APOL1 gene (e.g., an inversion in a 5' region of an APOL1 gene, e.g., an inversion in which the 5' region of an APOL1 gene is replaced with a 5' region of an APOL4 gene, such as the G3 allele).

Expression of these risk variants accounts for most of the increased risk of renal disease among African-Americans for several non-diabetic kidney diseases, including hypertension-associated kidney disease, focal segmental glomerulosclerosis, and HIV nephropathy (where the increase in risk is nearly 100 fold). A selective advantage of these polymorphisms also accounts for their high frequency. Individuals having these alleles experience increased protection against African sleeping sickness caused by the parasite Trypanosoma brucei rhodesiense. Whereas protection against sleeping sickness is a dominant trait, increased risk of renal disease behaves largely as a recessive trait. The compositions and methods described herein can be used to target these variant ApoL1 proteins and/or their biological effects. Such an approach can be used to protect patients with one or more susceptible genotypes against the associated increased risk of renal disease, e.g., end-stage renal disease, as well as other patients having or likely to develop renal disease.

ApoL1 has evolved recently under high selective pressure and is found only in humans and a few other primate species. ApoL1 has been extensively studied as a component of trypanolytic factor 1 (TLF-1), but almost nothing else is known about ApoL1 biology in higher primates. The few published papers document the presence of ApoL1 in HDL, but its function in this complex is unknown.

Expression of two or more risk-associated Apo-L1 variants increases disease risk between 10- and 100-fold. We believe this increase in risk represents one of the largest ever attributed to common variants. In this context we suggest that ApoL1-related kidney disease might be better characterized as a Mendelian disease with modifiers, rather than a common, complex disease.

Nephrologists have little to offer to their patients to slow the progression of diagnosed renal diseases, such as FSGS and ESKD. Current treatments include, e.g., angiotensin-converting enzyme inhibitors (ACEi) and angiotensin II receptor blockers (ARBs), but these treatments are non-specific and only moderately effective. Very few patients respond to steroids, and many of those only transiently.

We have discovered that agents that decrease the deleterious effects of pathogenic APOL1 high risk variants provide a beneficial therapy for patients having or that will progress to end-stage renal disease, as well as those patients that will likely require renal replacement therapy. In addition, the compositions and methods described herein also have application beyond renal disease, and can be used to treat patients having, e.g., cardiovascular disease, stroke, and/or peripheral vascular disease.

The compositions of the invention are well suited to targeted therapy, as they can be directed against a circulating factor (mutated APOL1) that appears to cause disease through gain-of-function mutations.

Susceptibility to kidney disease associated with the high-risk variants of APOL1 behaves like a recessive trait (Genovese et al., Science 329:841-845, 2010). For example, we observed that a human (age 51) with homozygous null APOL1 mutations that was identified after infection with the opportunistic pathogen Trypanosoma evansii displayed no evidence of either renal dysfunction or additional immune dysfunction. This suggests a gain-of-function phenotype of APOL1 renal risk variants despite recessive inheritance. In addition, heterozygotes appear not to develop renal disease, suggesting that the wild-type protein variant protects against coexpressed renal risk variants in APOL1 heterozygotes. Furthermore, the presence of two high-risk APOL1 alleles confers approximately 10-fold increased risk of FSGS and (in the context of HIV infection) approximately 100-fold increased risk of HIV nephropathy. Also, HDL3, which contains ApoL1, appears to be filtered by the glomerulus (Breznan et al., Biochem. J. 379:343-349, 2004), and APOL1 protein is immunodetected at high levels in proximal tubular epithelial cells, likely reflecting endocytic uptake of filtered HDL3, as well as in the glomerulus and renal vasculature. Among the six human ApoL gene products. APOL1 is the only secreted protein. Circulating APOL1 acts on trypanosomes via trypanosome receptor uptake and subsequent trafficking through the endosomal pathway to the lysosome. The high risk variants of APOL1 are similarly endocytosed from glomerular filtrate and the interstitial fluid by the kidney, and these processes appear to be required for accelerated progression of renal disease in affected individuals. In view of these observations, the invention provides compositions and methods for targeting and neutralizing APOL1 variants in patients having or likely to develop renal disease, which thereby treats or reduces the symptoms or likelihood of developing renal disease in patients at risk.

Compositions of the Invention

The compositions of the invention can be used to treat or prevent renal disease, or to ameliorate or reduce one or more symptoms of renal disease, in patients in need thereof (e.g., patients having one or more APOL1 risk alleles). The compositions of the invention include, e.g., an APOL1 polypeptide or fragment thereof, a nucleic acid molecule encoding an APOL1 polypeptide or fragment thereof, an anti-APOL1 antibody or fragment thereof, a nucleic acid molecule encoding an anti-APOL1 antibody or fragment thereof, an anti-APOL1 nucleic acid molecule (such as an antisense nucleobase oligomer or small RNA (e.g., an siRNA or RNAi molecule) that downregulates the expression of pathogenic APOL1), or an APOL1 protein antagonist (e.g., an SRA polypeptide that binds high risk pathogenic variants of APOL1, but does not bind (or binds at a substantially lower affinity to) common APOL1), as well as pharmaceutically acceptable excipients, diluents, and salts thereof.

Therapeutic APOL1 Polypeptides of the Invention

In a preferred embodiment, a composition of the invention that can be used to treat a disease condition (e.g., renal disease) includes a non-pathogenic APOL1 polypeptide ("common APOL1") that is not expressed from an APOL1 risk allele (e.g., the APOL1 polypeptide lacks one or more of the APOL1 gene mutations correlated with an increased risk of renal disease, such as the G1, G2, del6, and G3 mutations). The common APOL1 can be administered to a subject in need to counter the effects of an APOL1 polypeptide that is expressed from an APOL1 risk allele (a "pathogenic APOL1"). The recessive nature of APOL1 variant kidney disease risk suggests that administration of the common APOL1 would serve as a protein therapeutic by recapitulating the heterozygous state (e.g., in which the subject expresses at least one common APOL1 polypeptide (e.g., an APOL1 polypeptide that is encoded by a gene that is not expressed from an APOL1 risk allele (e.g., the gene does not include one or more of the G1, G2, del6, and/or G3 APOL1 gene mutations)) or by restoring to the subject a common APOL1 polypeptide or a fragment thereof at a level that is substantially similar to a subject that does not express, or expresses a non-disease causing level of, a pathogenic APOL1 polypeptide. A co-dominant or dominant suppressor mechanism would thereby reduce the elevated risk associated with unopposed action of circulating high risk pathogenic variants of APOL1. The therapeutic protein could be full length APOL1 (SEQ ID NO: 2), or a fragment thereof that does not include a mutation(s) correlated with an increased risk of renal disease, such as the G1, G2, del6, and G3 mutations. Preferably, an APOL1 fragment includes, e.g., all or a portion of the C-terminal coiled-coil domain of the common APOL1 polypeptide (e.g., at least amino acids 342-384 or at least amino acids 339-398). In other embodiments, an APOL1 polypeptide of the invention has at least 80% (e.g., at least 85%, 90%, 95%, 97%, 99%, or 100%) sequence identity over at least 25 (e.g., at least 50, 100, 150, 200, 250, 275, 300, 325, 350, or 398) contiguous amino acids of SEQ ID NO: 2. In a preferred embodiment, the APOL1 polypeptide of the invention has at least 95% sequence identity to the sequence of SEQ ID NO: 2.

The invention also features APOL1 polypeptide fragments that can be used to treat a disease condition (e.g., renal disease). For example, an APOL1 polypeptide fragment of the invention may include a sequence having at least 80% (e.g., at least 85%, 90%, 95%, 97%, 99%, or 100%) sequence identity to the sequence of any one of the following peptides shown in Table 1 below.

TABLE 1

| Polypeptide Sequences (SEQ ID NO: 2) | Polynucleotide Sequences (SEQ ID NO: 1) |
|---|---|
| a.a. 360-379 | n.a. 1080-1137 |
| a.a. 360-398 | n.a. 1080-1194 |
| a.a. 350-379 | n.a. 1050-1137 |
| a.a. 350-398 | n.a. 1050-1194 |
| a.a. 345-398 | n.a. 1035-1194 |
| a.a. 348-384 | n.a. 1044-1152 |
| a.a. 348-398 | n.a. 1044-1194 |
| a.a. 339-398 | n.a. 1017-1194 |
| a.a. 330-398 | n.a. 990-1194 |
| a.a. 320-398 | n.a. 960-1194 |
| a.a. 310-398 | n.a. 930-1194 |
| a.a. 300-398 | n.a. 900-1194 |
| a.a. 290-398 | n.a. 870-1194 |
| a.a. 280-398 | n.a. 840-1194 |
| a.a. 270-398 | n.a. 810-1194 |
| a.a. 260-398 | n.a. 780-1194 |

TABLE 1-continued

| Polypeptide Sequences (SEQ ID NO: 2) | Polynucleotide Sequences (SEQ ID NO: 1) |
|---|---|
| a.a. 250-398 | n.a. 750-1194 |
| a.a. 240-398 | n.a. 720-1194 |
| a.a. 238-398 | n.a. 714-1194 |
| a.a. 230-398 | n.a. 690-1194 |
| a.a. 220-398 | n.a. 660-1194 |
| a.a. 210-398 | n.a. 630-1194 |
| a.a. 200-398 | n.a. 600-1194 |
| a.a. 190-398 | n.a. 570-1194 |
| a.a. 180-398 | n.a. 540-1194 |
| a.a. 170-398 | n.a. 510-1194 |
| a.a. 160-398 | n.a. 480-1194 |
| a.a. 150-398 | n.a. 450-1194 |
| a.a. 140-398 | n.a. 420-1194 |
| a.a. 130-398 | n.a. 390-1194 |
| a.a. 120-398 | n.a. 360-1194 |
| a.a. 110-398 | n.a. 330-1194 |
| a.a. 100-398 | n.a. 300-1194 |
| a.a. 90-398 | n.a. 270-1194 |
| a.a. 80-398 | n.a. 240-1194 |
| a.a. 70-398 | n.a. 210-1194 |
| a.a. 60-398 | n.a. 180-1194 |
| a.a. 50-398 | n.a. 150-1194 |
| a.a. 40-398 | n.a. 120-1194 |
| a.a. 30-398 | n.a. 90-1194 |
| a.a. 20-398 | n.a. 60-1194 |
| a.a. 10-398 | n.a. 30-1194 |
| a.a. 339-390 | n.a. 1017-1170 |
| a.a. 339-380 | n.a. 1017-1140 |
| a.a. 339-370 | n.a. 1017-1110 |
| a.a. 339-360 | n.a. 1017-1080 |
| a.a. 339-350 | n.a. 1017-1050 |
| a.a. 320-390 | n.a. 960-1170 |
| a.a. 320-380 | n.a. 960-1140 |
| a.a. 320-370 | n.a. 960-1110 |
| a.a. 320-360 | n.a. 960-1080 |
| a.a. 320-350 | n.a. 960-1050 |
| a.a. 320-340 | n.a. 960-1020 |
| a.a. 320-330 | n.a. 960-990 |
| a.a. 310-390 | n.a. 930-1170 |
| a.a. 310-380 | n.a. 930-1140 |
| a.a. 310-370 | n.a. 930-1110 |
| a.a. 310-360 | n.a. 930-1080 |
| a.a. 310-350 | n.a. 930-1050 |
| a.a. 310-340 | n.a. 930-1020 |
| a.a. 310-330 | n.a. 930-990 |
| a.a. 310-320 | n.a. 930-960 |
| a.a. 304-398 | n.a. 912-1194 |
| a.a. 304-390 | n.a. 912-1170 |
| a.a. 304-380 | n.a. 912-1140 |
| a.a. 304-370 | n.a. 912-1110 |
| a.a. 304-360 | n.a. 912-1080 |
| a.a. 304-350 | n.a. 912-1050 |
| a.a. 304-340 | n.a. 912-1020 |
| a.a. 304-330 | n.a. 912-990 |
| a.a. 304-320 | n.a. 912-960 |
| a.a. 304-310 | n.a. 912-930 |
| a.a. 300-390 | n.a. 900-1170 |
| a.a. 300-380 | n.a. 900-1140 |
| a.a. 300-370 | n.a. 900-1110 |
| a.a. 300-360 | n.a. 900-1080 |
| a.a. 300-350 | n.a. 900-1050 |
| a.a. 300-340 | n.a. 900-1020 |
| a.a. 300-330 | n.a. 900-990 |
| a.a. 300-320 | n.a. 900-960 |
| a.a. 300-310 | n.a. 900-930 |
| a.a. 290-390 | n.a. 870-1170 |
| a.a. 290-380 | n.a. 870-1140 |
| a.a. 290-370 | n.a. 870-1110 |
| a.a. 290-360 | n.a. 870-1080 |
| a.a. 290-350 | n.a. 870-1050 |
| a.a. 290-340 | n.a. 870-1020 |
| a.a. 290-330 | n.a. 870-990 |
| a.a. 290-320 | n.a. 870-960 |
| a.a. 290-310 | n.a. 870-930 |
| a.a. 290-300 | n.a. 870-900 |
| a.a. 280-390 | n.a. 840-1170 |
| a.a. 280-380 | n.a. 840-1140 |

TABLE 1-continued

| Polypeptide Sequences (SEQ ID NO: 2) | Polynucleotide Sequences (SEQ ID NO: 1) |
|---|---|
| a.a. 280-370 | n.a. 840-1110 |
| a.a. 280-360 | n.a. 840-1080 |
| a.a. 280-350 | n.a. 840-1050 |
| a.a. 280-340 | n.a. 840-1020 |
| a.a. 280-330 | n.a. 840-990 |
| a.a. 280-320 | n.a. 840-960 |
| a.a. 280-310 | n.a. 840-930 |
| a.a. 280-300 | n.a. 840-900 |
| a.a. 280-290 | n.a. 840-870 |
| a.a. 270-390 | n.a. 810-1170 |
| a.a. 270-380 | n.a. 810-1140 |
| a.a. 270-370 | n.a. 810-1110 |
| a.a. 270-360 | n.a. 810-1080 |
| a.a. 270-350 | n.a. 810-1050 |
| a.a. 270-340 | n.a. 810-1020 |
| a.a. 270-330 | n.a. 810-990 |
| a.a. 270-320 | n.a. 810-960 |
| a.a. 270-310 | n.a. 810-930 |
| a.a. 270-300 | n.a. 810-900 |
| a.a. 270-290 | n.a. 810-870 |
| a.a. 270-280 | n.a. 810-840 |
| a.a. 260-390 | n.a. 780-1170 |
| a.a. 260-380 | n.a. 780-1140 |
| a.a. 260-370 | n.a. 780-1110 |
| a.a. 260-360 | n.a. 780-1080 |
| a.a. 260-350 | n.a. 780-1050 |
| a.a. 260-340 | n.a. 780-1020 |
| a.a. 260-330 | n.a. 780-990 |
| a.a. 260-320 | n.a. 780-960 |
| a.a. 260-310 | n.a. 780-930 |
| a.a. 260-300 | n.a. 780-900 |
| a.a. 260-290 | n.a. 780-870 |
| a.a. 260-280 | n.a. 780-840 |
| a.a. 260-270 | n.a. 780-810 |
| a.a. 250-390 | n.a. 750-1170 |
| a.a. 250-380 | n.a. 750-1140 |
| a.a. 250-370 | n.a. 750-1110 |
| a.a. 250-360 | n.a. 750-1080 |
| a.a. 250-350 | n.a. 750-1050 |
| a.a. 250-340 | n.a. 750-1020 |
| a.a. 250-330 | n.a. 750-990 |
| a.a. 250-320 | n.a. 750-960 |
| a.a. 250-320 | n.a. 750-960 |
| a.a. 250-310 | n.a. 750-930 |
| a.a. 250-300 | n.a. 750-900 |
| a.a. 250-290 | n.a. 750-870 |
| a.a. 250-280 | n.a. 750-840 |
| a.a. 250-270 | n.a. 750-810 |
| a.a. 250-260 | n.a. 750-780 |
| a.a. 240-390 | n.a. 720-1170 |
| a.a. 240-380 | n.a. 720-1140 |
| a.a. 240-370 | n.a. 720-1110 |
| a.a. 240-360 | n.a. 720-1080 |
| a.a. 240-350 | n.a. 720-1050 |
| a.a. 240-340 | n.a. 720-1020 |
| a.a. 240-330 | n.a. 720-990 |
| a.a. 240-320 | n.a. 720-960 |
| a.a. 240-320 | n.a. 720-960 |
| a.a. 240-310 | n.a. 720-930 |
| a.a. 240-300 | n.a. 720-900 |
| a.a. 240-290 | n.a. 720-870 |
| a.a. 240-280 | n.a. 720-840 |
| a.a. 240-270 | n.a. 720-810 |
| a.a. 240-260 | n.a. 720-790 |
| a.a. 240-250 | n.a. 720-760 |
| a.a. 238-390 | n.a. 714-1170 |
| a.a. 238-380 | n.a. 714-1140 |
| a.a. 238-370 | n.a. 714-1110 |
| a.a. 238-360 | n.a. 714-1080 |
| a.a. 238-350 | n.a. 714-1050 |
| a.a. 238-340 | n.a. 714-1020 |
| a.a. 238-330 | n.a. 714-990 |
| a.a. 238-320 | n.a. 714-960 |
| a.a. 238-320 | n.a. 714-960 |
| a.a. 238-310 | n.a. 714-930 |
| a.a. 238-300 | n.a. 714-900 |
| a.a. 238-290 | n.a. 714-870 |

TABLE 1-continued

| Polypeptide Sequences (SEQ ID NO: 2) | Polynucleotide Sequences (SEQ ID NO: 1) |
|---|---|
| a.a. 238-280 | n.a. 714-840 |
| a.a. 238-270 | n.a. 714-810 |
| a.a. 238-260 | n.a. 714-780 |
| a.a. 238-250 | n.a. 714-750 |

Preferably, the APOL1 polypeptide fragment includes a sequence having at least 95% sequence identity to amino acids 339-398 or amino acids 304-398 of SEQ ID NO: 2. In another preferred embodiment, the APOL1 polypeptide fragment includes the sequence of amino acids 339-398 or amino acids 238-398 of SEQ ID NO:2. In an embodiment, the APOL1 polypeptide therapeutics of the invention have sequences corresponding to the common APOL1 and do not have sequences identified as corresponding to an APOL1 risk allele (e.g., sequences corresponding to one or more mutations that result in a pathogenic APOL1 and correspond to an increased risk of renal disease in a subject).

Therapeutic APOL1 Nucleic Acid Molecules of the Invention

One or more of the APOL1 polypeptides or fragments thereof can also be administered to a patient in need of treatment for a disease (e.g., renal disease) as a nucleic acid molecule therapeutic. For example, the APOL1 can be administered as a nucleic acid molecule in a delivery vehicle.

Thus, the invention features compositions of the invention that include a delivery vector containing a nucleic acid molecule encoding an APOL1 polypeptide or fragment thereof (e.g., one or more of the nucleic acid sequences encoding APOL1 polypeptides described in Table 1 of the preceeding section. The compositions of the invention may be formulated for any route of administration (e.g., the administration routes described herein). The compositions of the invention may also further include secondary agents (either as a nucleic acid molecule to be expressed by a cell of the subject or as a polypeptide or drug) or they may be administered in combination with one or more additional therapeutic regimens (e.g., blood pressure medications, steroids, or immunosuppressive agents).

For example, the nucleic acid molecules of the invention have a nucleic acid sequence having at least 80% (e.g., at least 85%, 90%, 95%, 97%, 99%, or 100%) sequence identity to the nucleic acid sequences shown in Table 1 above. In an embodiment, the nucleic acid sequences encode APOL1 polypeptide therapeutics of the invention that have sequences corresponding to the common APOL1 and do not have sequences identified as corresponding to an APOL1 risk allele (e.g., sequences corresponding to one or more mutations that result in a pathogenic APOL1 and correspond to an increased risk of renal disease in a subject).

A delivery vehicle for the nucleic acid molecules of the invention can be a viral or non-viral vector. Any suitable viral vector system can be used including, e.g., adenoviruses (e.g., Ad2, Ad5, Ad9, Ad15, Ad17, Ad19, Ad20, Ad22, Ad26, Ad27, Ad28, Ad30, or Ad39; see, e.g., FIG. 2), rhabdoviruses (e.g., vesicular stomatitis virus), retroviruses (see, e.g., Miller, Curr. Top. Microbiol. Immunol. 158:1-24, 1992; Salmons and Gunzburg, Human Gene Therapy 4:129-141, 1993; and Miller et al., Methods in Enzymology 217:581-599, 1994), adeno-associated vectors (reviewed in Carter, Curr. Opinion Biotech. 3:533-539, 1992; and Muzcyzka, Curr. Top. Microbiol. Immunol. 158:97-129, 1992), poxviruses, herpes viral vectors, and Sindbis viral vectors (see viral vectors discussed generally in, e.g., Jolly, Cancer Gene Therapy 1:51-64, 1994; Latchman, Molec. Biotechnol. 2:179-195, 1994; Johanning et al., Nucl. Acids Res. 23:1495-1501, 1995; Berencsi et al., J. Infect. Dis. 183:1171-1179, 2001; Rosenwirth et al., Vaccine 19:1661-1670, 2001; Kittlesen et al., J. Immunol. 164:4204-4211, 2000; Brown et al., Gene Ther. 7:1680-1689, 2000; Kanesathasan et al., Vaccine 19:483-491, 2000; and Sten Drug 60:249-271, 2000. Compositions comprising such vectors and an acceptable excipient are also a feature of the invention.

Ad5 is a virus of the family Adenoviridae, species C, subtype 5. This virus is naturally occurring and causes mild upper respiratory infections, usually in children. Ad5 can be used as a delivery platform to deliver the genetic information to make human APOL1 in vivo. Typically, the Ad5 is rendered replication defective (by specific gene deletion; e.g., all or a portion of the E1 or E3 genes). Ad5 vectored vaccines have been approved for clinical studies widely in the past. Ad5 is widely used in clinical trials as a vector delivery system. As of June 2010, there are currently 29 clinical trials that are currently active using Ad5 vectored delivery of biologics/drugs. Adenovirus 5 based vectors exhibit an excellent safety profile. The Ad5 vector has additional benefits over conventional vaccines such as live-attenuated vaccines, a type of vaccine where pathogenic viruses are partially crippled via chemical or heat treatment prior to injection, in that there is no risk the Ad5 system could revert and cause illness. Further, Ad5 is a live vaccine which has been shown to provide prompt immunologic protection.

The viral vector may be constructed using conventional techniques known to one of skill in the art. For example, the viral vector may contain at least one sequence encoding a heterologous nucleic acid molecule (e.g., a nucleic acid molecule that encodes an APOL1 polypeptide or a fragment thereof), which is under the control of regulatory sequences that direct its expression in a cell. Appropriate amounts for vector-mediated delivery of the heterologous nucleic acid molecule can be readily determined by one of skill in the art. An increase in the expression level of a transfected nucleic acid molecule (e.g., a nucleic acid molecule that encodes an APOL1 polypeptide or a fragment thereof) in a host cell can be promoted by operably linking the nucleic acid molecule to an open frame expression control sequence, which can work in the selected expression host. Expression control sequences useful for eukaryotic host cells can be native or foreign to the nucleic acid molecule to be expressed, as well as to the delivery vector. Examples of expression control sequences include, but are not limited to, leader sequences, polyadenylation sequences, propeptide sequences, promoters, enhancers, upstream activation sequences, signal peptide sequences, and transcription termination factors. Expression control sequences include those derived from, e.g., SV40 (e.g., early and late promoters of SV40), bovine papilloma virus, adenovirus (e.g., early and late promoters of adenovirus), cytomegalovirus (CMV; e.g., the human cytomegalovirus early gene promoter), MT-1 (metallothioneine gene) promoter, Rous sarcoma virus (RSV) promoter, and human Ubiquitine C (UbC) promoter. In order to further improve expression in mammalian cells, synthetic intron sequences can be inserted into a non-transcription region of a nucleotide sequence encoding the APOL1 polypeptide.

Other vector components that can be used in practicing the present invention include a signal peptide. This sequence is typically located at the 5' of a gene encoding a protein and is thus added to the amino terminus of the protein during expression. The presence or absence of a signal peptide varies depending on the expression host cell to be used in production of the APOL1 polypeptide or fragment thereof and the preference of producing a secreted product (i.e., according to whether the APOL1 polypeptide is to be expressed intra-cellularly or extra-cellularly). In an embodiment, the APOL1 polypeptide or fragment thereof is secreted from the host cell during expression. The signal peptide can be homologous or heterologous to either the APOL1 polypeptide (or fragment thereof) or the host cell.

A nucleic acid molecule is "operably linked" to another nucleic acid molecule when they are arranged in a functional relationship. This means that an appropriate molecule (for example, a transcription activator) binds to a regulatory sequence(s), a gene, or a regulatory sequence (s) linked in such a way that the expression of the nucleic acid molecule is modulated. For example, when a pre-sequence or secretory leader participates in secretion of a mature protein, they are operably linked to the promoter. When a promoter affects transcription of a coding sequence, the promoter is operably linked to the coding sequence. When a ribosomal binding site is located at a place capable of being read as a coding sequence, the ribosomal binding site is operably linked to the coding sequence. Generally "operably linked" means in contact with a linked nucleic acid molecule and a secretory leader and to be in a reading frame.

Non-viral approaches can also be employed to introduce a therapeutic nucleic acid molecule (e.g., a nucleic acid molecule encoding an APOL1 polypeptide or a fragment thereof) into cells to treat or prevent renal disease or one or more symptoms thereof. For example, a heterologous nucleic acid molecule (e.g., a nucleic acid molecule that encodes an APOL1 polypeptide or fragment thereof can be introduced into a cell by lipofection (see, e.g., Felgner et al., Proc. Natl. Acad. Sci. USA 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (see, e.g., Wu et al., Journal of Biological Chemistry 263:14621, 1988; Wu et al., Journal of Biological Chemistry 264:16985, 1989), or, less preferably, microinjection under surgical conditions (see, e.g., Wolff et al., Science 247:1465, 1990). Gene transfer can also be achieved by the use of calcium phosphate, DEAE dextran, electroporation, and protoplast fusion. Liposomes, microparticles, or nanoparticles can also be potentially beneficial for delivery of a nucleic acid molecule (e.g., a nucleic acid molecule that encodes an APOL1 polypeptide or fragment thereof) or a protein into a cell or into a patient in order to treat or prevent a renal disease or one or more symptoms of renal disease. Other non-viral methods of delivering a nucleic acid molecule that encodes an APOL1 polypeptide or fragment thereof is described in, e.g., Coleman et al., Hum. Gene Ther. 9:2223-2230, 1998, and Horton et al., Proc. Natl. Acad. Sci. USA 96:1553-1558, 1999).

An ex vivo strategy can also be used for therapeutic applications. Ex vivo strategies involve transfecting or transducing cells obtained from the subject with a nucleic acid molecule. The transfected or transduced cells are then returned to the subject. The ex vivo methods include the steps of, e.g., harvesting cells from a subject, culturing the cells, transducing them with an expression vector, and maintaining the cells under conditions suitable for expression of the nucleic acid molecule or functional fragment. These methods are known in the art of molecular biology. The transduction step is accomplished by any standard means used for ex vivo gene therapy including, e.g., calcium phosphate, lipofection, electroporation, viral infection, and biolistic gene transfer. Alternatively, liposomes or polymeric microparticles can be used. Cells that have been successfully transduced can then be selected, for example, for expression of the coding sequence or of a drug resistance gene. The cells may then be lethally irradiated (if desired) and injected or implanted into the patient.

Therapeutic RNA Interference Agents of the Invention that Target Expression of APOL1

The present invention also features therapeutic ribonucleic acid interference agents (RNAi) that can be used to decrease the levels of APOL1 polypeptide expression (e.g., a pathogenic APOL1) in a cell for the treatment of disease (e.g., a renal disease). Such therapeutic RNAi agents include, e.g., antisense nucleobase oligomers, microRNAs, dsRNA, or small interfering RNAs that downregulate expression of APOL1 mRNA directly.

In preferred embodiments, the RNAi agents of the invention include nucleic acid molecules with sequences that are complementary to sequences having at least 80% (e.g., at least 85%, 90%, 95%, 97%, 99%, or 100%) sequence identity to the nucleic acid sequences shown in Table 1 above. Preferably, the RNAi agents include sequences that are complementary to sequences present in an APOL1 risk allele and that correspond to an increased risk of renal disease. Accordingly, the RNAi agents can be used to down-regulate or reduce expression of pathogenic APOL1 polypeptides, but will not substantially down-regulate or reduce expression of common APOL1 polypeptides (e.g., preferably, the RNAi agents reduce expression of pathogenic APOL1 by at least about 20%, 30%, 40%, 50%, 60%, 70%, 80%, 90%, 95%, or 99% or more, but reduce expression of common APOL1 by less than 70%, 60%, 50%, 40%, 30%, 20%, 10%, 5%, or less). In an embodiment, the nucleic acid sequences of the RNAi agents are complementary to the nucleic acid sequences shown in Table 1 above except that the nucleic acid sequences include one or more mutations associated with an APOL1 risk allele (e.g., the G1, G2, del6, and/or G3 mutations). In other embodiments, the complementary nucleic acid sequences are interfering RNAs (e.g., microRNAs, siRNAs, dsRNAs, and antisense RNAs) that can be used to downregulate or reduced expression of pathogenic APOL1 polypeptides relative to common APOL1.

By binding to the complementary nucleic acid sequence (e.g., the sense or coding strand) of a pathogenic APOL1 mRNA, RNAi agents are able to inhibit or reduce pathogenic APOL1 protein expression, presumably through the enzymatic cleavage of the RNA strand by RNAse H. Preferably, the RNAi agents are capable of reducing pathogenic APOL1 protein expression in a cell. Preferably, the decrease in pathogenic APOL1 expression is at least 10% relative to cells treated with a control RNAi agent, preferably 20% or greater, more preferably 40%, 50%, 60%, 70%, 80%, 90%, 95%, 99% or greater. Methods for selecting and preparing pathogenic APOL1 RNAi agents are well known in the art. Methods for assaying levels of protein expression are also well known in the art and include, e.g., Western blotting, immunoprecipitation, and ELISA.

RNA Interference Agents

While the first described RNAi molecules were RNA:RNA hybrids comprising both an RNA sense and an RNA antisense strand, it has now been demonstrated that DNA sense:RNA antisense hybrids, RNA sense:DNA antisense hybrids, and DNA:DNA hybrids are capable of mediating RNAi (Lamberton et al., Molec. Biotechnol. 24:111-119, 2003). Thus, the invention includes the use of RNAi molecules comprising any of these different types of double-stranded molecules, which can be used to reduce expression of a pathogenic APOL1. In addition, it is understood that RNAi molecules may be used and introduced to cells in a variety of forms. Accordingly, as used herein, RNAi molecules encompasses any and all molecules capable of inducing an RNAi response in cells, including, but not limited to, double-stranded polynucleotides comprising two separate strands, i.e. a sense strand and an antisense strand, e.g., small interfering RNA (siRNA); polynucleotides comprising a hairpin loop of complementary sequences, which forms a double-stranded region, e.g., shRNAi molecules, and expression vectors that express one or more polynucleotides capable of forming a double-stranded polynucleotide alone or in combination with another polynucleotide.

RNA interference (RNAi) may be used to specifically inhibit expression of target polynucleotides (e.g., pathogenic APOL1 polynucleotides, but preferably not common APOL1). Double-stranded RNA-mediated suppression of gene and nucleic acid expression may be accomplished according to the invention by introducing dsRNA, siRNA or shRNA into cells or organisms. SiRNA may be double-stranded RNA, or a hybrid molecule comprising both RNA and DNA, e.g., one RNA strand and one DNA strand. It has been demonstrated that the direct introduction of siRNAs to a cell can trigger RNAi in mammalian cells (Elshabir et al., Nature 411:494-498, 2001). Furthermore, suppression in mammalian cells occurred at the RNA level and was specific for the targeted genes, with a strong correlation between RNA and protein suppression (Caplen et al., Proc. Natl. Acad. Sci. USA 98:9746-9747, 2001). In addition, it was shown that a wide variety of cell lines, including HeLa S3, COS7, 293, NIH/3T3, A549, HT-29, CHO-KI and MCF-7 cells, are susceptible to some level of siRNA silencing (Brown et al., TechNotes 9(1):1-7, 2002).

Exemplary RNAi agents include siRNA, shRNA, dsRNA, and miRNA agents. In certain embodiments, the RNAi agent is a small interfering RNA (siRNA). These are short (usually 21 nt) and are usually double-stranded RNA (dsRNA). siRNA molecules may have, for example, 1 or 2 nucleotide overhangs on the 3' ends, or may be blunt-ended. Each strand has a 5' phosphate group and a 3' hydroxyl group. Most siRNA molecules are 18 to 30 (e.g., 21 to 30) nucleotides in length, however a skilled practitioner may vary this sequence length (e.g., to increase or decrease the overall level of gene silencing).

Almost any gene for which the sequence is known can thus be targeted based on sequence complementarity with an appropriately tailored siRNA. See, for example, Zamore et al., Cell 101:25-33, 2000; Bass, Nature 411:428-429, 2001; Elbashir et al., Nature 411:494-498, 2001; and PCT Publication Nos. WO 00/44895, WO 01/36646, WO 99/32619, WO 00/01846, WO 01/29058, WO 99/07409, and WO 00/44914. Methods for preparing a siRNA molecule are known in the art and described in, for example, U.S. Pat. No. 7,078,196. Accordingly, one of skill in the art would understand that a wide variety of different siRNA molecules may be used to target a specific gene or transcript. In certain embodiments, siRNA molecules according to the invention are double-stranded and 16-30 or 18-25 nucleotides in length, including each integer in between. In one embodiment, an siRNA is 21 nucleotides in length. In certain embodiments, siRNAs have 0-7 nucleotide 3' overhangs or 0-4 nucleotide 5' overhangs. In one embodiment, a siRNA molecule has a two nucleotide 3' overhang. In one embodiment, a siRNA is 21 nucleotides in length with two nucleotide 3' overhangs (e.g., they contain a 19 nucleotide complementary region between the sense and antisense strands). In certain embodiments, the overhangs are UU or dTdT 3' overhangs.

Generally, siRNA molecules are completely complementary to one strand of a target DNA molecule, since even single base pair mismatches have been shown to reduce silencing. In other embodiments, siRNAs may have a modified backbone composition, such as, for example, 2'-deoxy- or 2'-O-methyl modifications. However, in preferred embodiments, the entire strand of the siRNA is not made with either 2' deoxy or 2'-O-modified bases. In one embodiment, siRNA target sites are selected by scanning the target mRNA transcript sequence for the occurrence of AA dinucleotide sequences. Each AA dinucleotide sequence in combination with the 3' adjacent approximately 19 nucleotides are potential siRNA target sites. In one embodiment, siRNA target sites are preferentially not located within the 5' and 3' untranslated regions (UTRs) or regions near the start codon (within approximately 75 bases), since proteins that bind regulatory regions may interfere with the binding of the siRNP endonuclease complex (Elshabir et al., Nature 411: 494-498, 2001; Elshabir et al., EMBO J. 20:6877-6888, 2001). In addition, potential target sites may be compared to an appropriate genome database, such as BLASTN 2.0.5, and potential target sequences with significant homology to other coding sequences eliminated.

A short hairpin RNA (shRNA) molecule may also be used in the invention. shRNA are single-stranded RNA molecules in which a tight hairpin loop structure is present, allowing complementary nucleotides within the same strand to form bonds. shRNA can exhibit reduced sensitivity to nuclease degradation as compared to siRNA. Once inside a target cell, shRNA are processed and effect gene silencing by the same mechanism described above for siRNA. In certain embodiments, they may contain variable stem lengths, typically from 19 to 29 nucleotides in length, or any number in between. In certain embodiments, hairpins contain 19 to 21 nucleotide stems, while in other embodiments, hairpins contain 27 to 29 nucleotide stems. In certain embodiments, loop size is between 4 to 23 nucleotides in length, although the loop size may be larger than 23 nucleotides without significantly affecting silencing activity. ShRNA molecules may contain mismatches, for example G-U mismatches between the two strands of the shRNA stem without decreasing potency. In certain embodiments, shRNAs are designed to include one or several G-U pairings in the hairpin stem to stabilize hairpins during propagation in bacteria, for example. However, complementarity between the portion of the stem that binds to the target mRNA (antisense strand) and the mRNA is typically required, and even a single base pair mismatch is this region may abolish silencing. 5' and 3' overhangs are not required, since they do not appear to be critical for shRNA function, although they may be present (Paddison et al., Genes & Dev. 16(8):948-958, 2002).

Double-stranded RNA (dsRNA) can also be used in the invention. Any double-stranded RNA that can be cleaved in cell into siRNA molecules that target a specific mRNA can be used. Methods of preparing dsRNA for use as RNAi agents are described in, for example, U.S. Pat. No. 7,056, 704.

MicroRNAs (miRNA) can also be used in the invention. miRNA are single-stranded RNA molecules that can silence a target gene using the same or similar mechanisms as siRNA and shRNA agents. miRNA molecules of 17 to 25 (e.g., 21 to 23) nucleotides in length are often used, as these are generally the most effective for gene silencing; however, a skilled practitioner may vary the sequence length as desired.

In one embodiment, a nucleic acid is an antisense oligonucleotide directed to a target polynucleotide. Antisense oligonucleotides are single strands of DNA or RNA that are complementary to a chosen sequence. In the case of antisense RNA, they prevent translation of complementary RNA strands by binding to it. Antisense DNA can be used to target a specific, complementary (coding or non-coding) RNA. If binding takes places this DNA/RNA hybrid can be degraded by the enzyme RNase H. In particular embodiment, antisense oligonucleotides contain from about 10 to about 50 nucleotides, more preferably about 15 to about 30 nucleotides. The term also encompasses antisense oligonucleotides that may not be exactly complementary to the desired target gene. Thus, the invention can be utilized in instances where non-target specific-activities are found with antisense, or where an antisense sequence containing one or more mismatches with the target sequence is the most preferred for a particular use.

Antisense oligonucleotides have been demonstrated to be effective and targeted inhibitors of protein synthesis, and, consequently, can be used to specifically inhibit protein synthesis by a targeted gene (e.g., a pathogenic APOL1 polypeptide, but preferably not a common APOL1 polypeptide). The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (U.S. Pat. Nos. 5,739,119 and 5,759,829). Further, examples of antisense inhibition have been demonstrated with the nuclear protein cyclin, the multiple drug resistance gene (MDG1), ICAM-1, E-selectin, STK-1, striatal GABAA receptor and human EGF (see e.g., Jaskulski et al., Science 240(4858):1544-1546, 1988; Vasanthakumar et al., Cancer Commun. 1(4):225-232, 1989; Peris et al., Brain Res Mol Brain Res. 57(2):310-20, 1998; and U.S. Pat. Nos. 5,801, 154; 5,789,573; 5,718,709; and 5,610,288). Furthermore, antisense constructs have also been described that inhibit and can be used to treat a variety of abnormal cellular proliferations, e.g. cancer (U.S. Pat. Nos. 5,747,470; 5,591, 317; and 5,783,683).

Methods of producing antisense oligonucleotides are known in the art and can be readily adapted to produce an antisense oligonucleotide that targets any polynucleotide sequence. Selection of antisense oligonucleotide sequences specific for a given target sequence is based upon analysis of the chosen target sequence and determination of secondary structure, Tm, binding energy, and relative stability. Antisense oligonucleotides may be selected based upon their relative inability to form dimers, hairpins, or other secondary structures that would reduce or prohibit specific binding to the target mRNA in a host cell. Highly preferred target regions of the mRNA include those regions at or near the AUG translation initiation codon and those sequences that are substantially complementary to 5' regions of the mRNA. These secondary structure analyses and target site selection considerations can be performed, for example, using v.4 of the OLIGO primer analysis software (Molecular Biology Insights) and/or the BLASTN 2.0.5 algorithm software (Altschul et al., Nucleic Acids Res. 25(17):3389-3402, 1997).

According to another embodiment of the invention, nucleic acid-lipid particles can be associated with ribozymes. Ribozymes are RNA-protein complexes having specific catalytic domains that possess endonuclease activity (Kim et al., Proc Natl Acad Sci USA 84(24):8788-8792, 1987; Forster et al., Cell 49(2):211-220, 1987). For example, a large number of ribozymes accelerate phosphoester transfer reactions with a high degree of specificity, often cleaving only one of several phosphoesters in an oligonucleotide substrate. This specificity has been attributed to the requirement that the substrate bind via specific base-pairing interactions to the internal guide sequence ("IGS") of the ribozyme prior to chemical reaction. The enzymatic nucleic acid molecule may be formed in a hammerhead, hairpin, a hepatitis 6 virus, group I intron or RNaseP RNA (in association with an RNA guide sequence) or Neurospora VS RNA motif, for example. Specific examples of hammerhead motifs are described by Rossi et al., Nucleic Acids Res. 20(17):4559-4565, 1992. Examples of hairpin motifs are described by Hampel et al. (Eur. Pat. Appl. Publ. No. EP 0360257), Hampel et al., Biochemistry 28(12):4929-4933, 1989; Hampel et al., Nucleic Acids Res. 18(2):299-304, 1990, and U.S. Pat. No. 5,631,359; and an example of the Group I intron is described in U.S. Pat. No. 4,987,071. Ribozymes may be designed as described in Int. Pat. Appl. Publ. No. WO 93/23569 and Int. Pat. Appl. Publ. No. WO 94/02595, each specifically incorporated herein by reference, and synthesized to be tested in vitro and in vivo, as described therein. Ribozyme activity can be optimized by altering the length of the ribozyme binding arms or chemically synthesizing ribozymes with modifications that prevent their degradation by serum ribonucleases (see e.g., Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem loop bases to shorten RNA synthesis times and reduce chemical requirements.

Nucleic acids associated with lipid particles of the present invention may be immunostimulatory, including immunostimulatory oligonucleotides (ISS; single- or double-stranded) capable of inducing an immune response when administered to a subject, which may be a mammal or other patient. ISS include, e.g., certain palindromes leading to hairpin secondary structures (see Yamamoto et al., J. Immunol. 148: 4072-4076, 1992), or CpG motifs, as well as other known ISS features (such as multi-G domains, see WO 96/11266). In one embodiment, the immunostimulatory nucleic acid or oligonucleotide comprises at least one CpG dinucleotide. The oligonucleotide or CpG dinucleotide may be unmethylated or methylated. In another embodiment, the immunostimulatory nucleic acid comprises at least one CpG dinucleotide having a methylated cytosine. In one embodiment, the nucleic acid comprises a single CpG dinucleotide, wherein the cytosine in said CpG dinucleotide is methylated. In a specific embodiment, the nucleic acid comprises the sequence 5' TAACGTTGAGGGGCAT 3'. In an alternative embodiment, the nucleic acid comprises at least two CpG dinucleotides, wherein at least one cytosine in the CpG dinucleotides is methylated. In a further embodiment, each cytosine in the CpG dinucleotides present in the sequence is methylated. In another embodiment, the nucleic acid comprises a plurality of CpG dinucleotides, wherein at least one of said CpG dinucleotides comprises a methylated cytosine.

Additional specific nucleic acid sequences of oligonucleotides (ODNs) suitable for use in the compositions and methods of the invention are described in U.S. Patent Application Pub. Nos. 2005/0249794 and 2004/0013649, Int. Publ. Nos. WO 02/069369 and WO 01/15726, U.S. Pat. No. 6,406,705, and Raney et al., J. Pharmacol. Exp. Therap. 298:1185-1192, 2001). In certain embodiments, ODNs used in the compositions and methods of the present invention have a phosphodiester ("PO") backbone or a phosphorothioate ("PS") backbone, and/or at least one methylated cytosine residue in a CpG motif.

A variety of methods are available for the introduction (e.g., transfection) of nucleic acid molecules (e.g., RNAi agents) into mammalian cells. For example, there are several commercially-available transfection reagents useful for lipid-based transfection of siRNAs including, but not limited to, TransIT-TKO™ (Mirus, Catalog No. MIR 2150), Transmessenger™ (Qiagen, Catalog No. 301525), Oligofectamine™ and Lipofectamine™ (Invitrogen, Catalog No. MIR 12252-011 and Catalog No. 13778-075), siPORT™ (Ambion, Catalog No. 1631), and DharmaFECT™ (Fisher Scientific, Catalog No. T-2001-01). Agents are also commercially available for electroporation-based methods for transfection of siRNA, such as siPORTer™ (Ambion, Catalog No. 1629). Microinjection techniques may also be used. The nucleic acid molecule may also be transcribed from an expression construct introduced into the cells, where the expression construct includes a coding sequence for transcribing the nucleic acid molecule operably linked to one or more transcriptional regulatory sequences. Where desired, plasmids, vectors, or viral vectors can also be used for the delivery of the nucleic acid molecule, and such vectors are known in the art. Additional methods are known in the art and are described, for example, in U.S. Patent Application Publication No. 2006/0058255.

Any of the RNAi molecules described herein may be modified or substituted with nucleotide analogs, e.g., as described herein. RNAi agents may be capable of silencing any gene where a reduction in expression of that gene is therapeutically beneficial.

Modified Nucleic Acids for Use in the RNAi Molecules of the Invention

Modified nucleic acids, including modified DNA or RNA molecules, may be used in the in place of naturally occurring nucleic acids in the RNAi polynucleotides described herein. Modified nucleic acids can improve the half-life, stability, specificity, delivery, solubility, and nuclease resistance of the polynucleotides described herein. For example, siRNA agents can be partially or completed composed of nucleotide analogs that confer the beneficial qualities described above. As described in Elmén et al. (Nucleic Acids Res. 33:439-447, 2005), synthetic, RNA-like nucleotide analogs (e.g., locked nucleic acids (LNA)) can be used to construct siRNA molecules that exhibit silencing activity against a target gene product.

Modified nucleic acids include molecules in which one or more of the components of the nucleic acid, namely sugars, bases, and phosphate moieties, are different from that which occurs in nature, preferably different from that which occurs in the human body. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone.

Antisense, siRNA, and other oligonucleotides useful in this invention include, but are not limited to, oligonucleotides containing modified backbones or non-natural internucleoside linkages. Oligonucleotides having modified backbones include those that retain a phosphorus atom in the backbone and those that do not have a phosphorus atom in the backbone. Modified oligonucleotides that do not have a phosphorus atom in their internucleoside backbone can also be considered to be oligonucleosides. Modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, phosphoroselenate, methylphosphonate, or O-alkyl phosphotriester linkages, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included. Representative United States patents that teach the preparation of the above linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

In certain embodiments, modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include, e.g., those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative United States patents that describe the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

The phosphorothioate backbone modification, where a non-bridging oxygen in the phosphodiester bond is replaced by sulfur, is one of the earliest and most common means deployed to stabilize nucleic acid drugs against nuclease degradation. In general, it appears that PS modifications can be made extensively to both siRNA strands without much impact on activity (Kurreck, Eur. J. Biochem. 270:1628-44, 2003). In particular embodiments, the PS modification is usually restricted to one or two bases at the 3' and 5' ends. The boranophosphate linker can be used to enhance siRNA activity while having low toxicity (Hall et al., Nucleic Acids Res. 32:5991-6000, 2004).

Other useful nucleic acids derivatives include those nucleic acids molecules in which the bridging oxygen atoms (those forming the phosphoester linkages) have been replaced with —S—, —NH—, —$CH_2$—, and the like. In certain embodiments, the alterations to the antisense, siRNA, or other nucleic acids used will not completely affect the negative charges associated with the nucleic acids. Thus, the present invention contemplates the use of antisense, siRNA, and other nucleic acids in which a portion of the linkages are replaced with, for example, the neutral methyl phosphonate or phosphoramidate linkages. When neutral linkages are used, in certain embodiments, less than 80% of the nucleic acid linkages are so substituted, or less than 50% of the linkages are so substituted.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Certain nucleobases are particularly useful for increasing the binding affinity of the oligomeric compounds of the invention, including 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications 1993, CRC Press, Boca Raton, pages 276-278). These may be combined, in particular embodiments, with 2'-O-methoxyethyl sugar modifications. United States patents that teach the preparation of certain of these modified nucleobases as well as other modified nucleobases include, but are not limited to, the above noted U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941.

Exemplary sugar modifications include modifications to the 2'-OH of the RNA sugar ring, which provides a convenient chemically reactive site. Exemplary modifications include the 2'-F and 2'-OMe modification, which can be restricted to less than 4 nucleotides per strand (Holen et al., Nucleic Acids Res 31:2401-2407, 2003). The 2'-O-MOE is most effective in siRNA when modified bases are restricted to the middle region of the molecule (Prakash et al., J. Med. Chem. 48:4247-4253, 2005).

Modified oligonucleotides may also contain one or more substituted sugar moieties. For example, the invention includes oligonucleotides that comprise one of the following at the 21 position: OH; F; O-, S-, or N-alkyl, O-alkyl-O-alkyl, O-, S-, or N-alkenyl, or O-, S- or N-alkynyl, wherein the alkyl, alkenyl and alkynyl may be substituted or unsubstituted $C_{1-10}$ alkyl or $C_{2-10}$ alkenyl and alkynyl. Particularly preferred are $O[CH_2)_nO]_mCH_3$, $O(CH_2)_nOCH_3$, $O(CH_2)_2ON(CH_3)_2O(CH_2)_nNH_2$, $O(CH_2)_nCH_3$, $O(CH_2)_nONH_2$, and $O(CH_2)_nON[(CH_2)_nCH_3)]$—, where n and m are from 1 to about 10. Other preferred oligonucleotides comprise one of the following at the 2' position: $C_{1-10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy (2'-O—$CH_2CH_2OCH_3$, also known as 2'-O-(2-methoxyethyl) or 2'-MOE) (Martin et al., Helv. Chim. Acta 78:486-504, 1995), i.e., an alkoxyalkoxy group. Other modifications include 2'-dimethylaminooxyethoxy, i.e., a $O(CH_2)_2ON(CH_3)_2$ group, also known as 2'-DMAOE, and 2'-dimethylaminoethoxyethoxy (2'-DMAEOE). Additional modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920.

In other oligonucleotide mimetics, both the sugar and the internucleoside linkage, i.e., the backbone, of the nucleotide units are replaced with novel groups, although the base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262. Further teaching of PNA compounds can be found in Nielsen et al., Science 254, 1497-1500 (1991).

Particular embodiments of the invention are oligonucleotides with phosphorothioate backbones and oligonucleosides with heteroatom backbones, and in particular $CH_2NHOCH_2$, $CH_2N(CH_3)OCH_2$— (referred to as a methylene(methylimino) or MMI backbone), $CH_2ON(CH_3)CH_2$, $CH_2N(CH_3)N(CH_3)CH_2$, and $ON(CH_3)CH_2CH_2$ (wherein the native phosphodiester backbone is represented as $OPOCH_2$) of U.S. Pat. No. 5,489,677; the amide backbones of U.S. Pat. No. 5,602,240; and the morpholino backbone structures U.S. Pat. No. 5,034,506.

Therapeutic Anti-APOL1 Antibodies and Antibody Fragments of the Invention

The invention also features substantially isolated anti-APOL1 antibodies and fragments thereof that can bind and neutralize APOL1 polypeptide. In an embodiment, the anti-APOL1 antibodies preferably bind to pathogenic APOL1 relative to their binding to common APOL1 (e.g., the anti-APOL1 antibodies preferentially bind to pathogenic APOL1 and exhibit a reduced binding preference for (or little or no binding to) common APOL1. For example, the anti-APOL1 antibodies specifically bind to pathogenic APOL1 with a dissociation constant of, e.g., less than $10^{-6}$ M, more preferably less than $10^{-7}$ M, $10^{-8}$ M, $10^{-9}$ M, $10^{-10}$ M, $10^{-11}$ M, or $10^{-12}$ M, and most preferably less than $10^{-13}$ M, $10^{-14}$ M or $10^{-15}$ M, and bind to common APOL1 with a dissociation constant at least 1 order of magnitude, preferably at least 2, 3, 4, or 5 orders of magnitude lower.

The antibodies can bind to and neutralize a common variant of APOL1 or a pathogenic variant of APOL1. By promoting clearance of APOL1 from the circulation through Fc-receptors or other nonspecific pathways, such an antibody would lower the concentration of the circulating APOL1 renal risk variant. The APOL1 immune complex would be routed into a non-pathogenic degradation pathway.

In a preferred embodiment, the antibody (e.g., a human antibody or a humanized monoclonal antibody) has specificity for a high-risk variant of APOL1 (e.g., a variant having the G1, G2, del6, and/or G3 mutations), and does not recognize a common APOL1. Such an antibody would potentially serve a dual purpose. It would remove high-risk APOL1 variants from the circulation of a patient in need, and it would be compatible with co-administration of common APOL1 polypeptide or fragment thereof (or a nucleic acid molecule encoding an APOL1 polypeptide or fragment thereof). Examples of an anti-APOL1 antibody that is capable of binding to a pathogenic APOL1 include those antibodies that bind an epitope that includes the G1 mutation (S342G) and/or an epitope that includes the G2 mutation (I384M) and/or an epitope of APOL1 that lacks amino acids N388 and Y389 (i.e., the del6 mutation, which removes amino acids N388 and Y389 of APOL1) and/or an epitope that includes the G3 mutation (i.e., an epitope that results upon expression of an APOL4/APOL1 hybrid gene due to inversion of a segment of DNA including the 5' end of APOL4, all of APOL2, and the 5' end of APOL1).

Other anti-APOL1 antibodies of the invention include those antibodies capable of binding an epitope of an APOL1 polypeptide within a region of one or more of the peptides shown in Table 1 above. Other preferred anti-APOL1 antibodies or fragments thereof bind to surface exposed amino acids residues. Preferably, the anti-APOL1 antibodies of the invention have high binding affinity or specific binding (e.g., a dissociation constant of, e.g., less than $10^{-6}$ M, more preferably less than $10^{-7}$ M, $10^{-8}$ M, $10^{-9}$ M, $10^{-10}$ M, $10^{-11}$ M, or $10^{-12}$ M, and most preferably less than $10^{-13}$ M, $10^{-14}$ M or $10^{-15}$ M.

In other preferred embodiments, an antibody therapeutic of the invention specifically binds to the carboxy-terminus of an APOL1 polypeptide (e.g., a region that includes amino acids 339-398 of SEQ ID NO: 2) and inhibits or reduce its interaction with, e.g., HDL3.

The development of antibodies is well understood in the art. In particular, the antibodies of the invention antagonize APOL1. In a preferred embodiment, the anti-APOL1 antibodies do not independently induce apoptosis or ADCC. Such antibodies can be modified so that they do not directly interact with complement. For example, the antibodies might lack the Fc region (e.g., Fabs), or the Fc region can be modified (e.g., through mutation) not to interact with complement.

An example of anti-APOL1 antibody is ID4 (Cat. #NBP1-28866; Novus Biologicals, Littleton, Colo.; and Cat. #LS-C108770; LifeSpan BioSciences). This antibody can be humanized for use in methods of treating human patients.

The invention also features anti-APOL1 monoclonal and polyclonal antibodies. Methods for the generation of monoclonal and polyclonal antibodies are known in the art. These methods include the immunological method described by Kohler and Milstein (Nature 256: 495-497, 1975), Kohler and Milstein (Eur. J. Immunol. 6: 511-519, 1976), and Campbell ("Monoclonal Antibody Technology, The Production and Characterization of Rodent and Human Hybridomas" in Burdon et al., Eds., Laboratory Techniques in Biochemistry and Molecular Biology, Volume 13, Elsevier Science Publishers, Amsterdam, 1985), as well as by the recombinant DNA method described by Huse et al. (Science 246: 1275-1281, 1989). While the preferred animal for producing monoclonal antibodies may be a mouse, the invention is not so limited; in fact, human antibodies may be used and may prove to be preferable. Such antibodies can be obtained by using human hybridomas (Cole et al., Monoclonal Antibodies and Cancer Therapy, Alan R. Liss Inc., p. 77-96, 1985).

Murine myeloma cell lines useful for the production of monoclonal antibodies can be obtained, for example, from the American Type Culture Collection (ATCC; Manassas, Va.). Human myeloma and mouse-human heteromyeloma cell lines have also been described (Kozbor et al., J. Immunol., 133:3001-3005, 1984; Brodeur et al., Monoclonal Antibody Production Techniques and Applications, Marcel Dekker, Inc., New York, pp. 51-63, 1987).

Human antibodies can also be produced using various techniques known in the art, including phage display libraries (Marks et al., J. Mol. Biol., 222:581-597, 1991, Winter et al. Annu. Rev. Immunol., 12:433-455, 1994, and Smith et al., supra). The techniques of Cole et al. and Boerner et al. are also useful for the preparation of human monoclonal antibodies (Cole et al., supra; Boerner et al., J. Immunol., 147: 86-95, 1991).

The antibody of the invention may be prepared in any mammal, including mice, rats, rabbits, goats, camels, and humans. The antibody or functional fragment thereof may be a member of one of the following immunoglobulin classes: IgG, IgM, IgA, IgD, or IgE, and the subclasses thereof, and preferably is an IgG antibody or fragment thereof. Antibodies or antibody fragments of the invention, as used herein, contain one or more complementarity determining regions (CDR) or binding peptides that bind to APOL1 (e.g., APOL1 protein that includes one or mutations associated with an increased risk of renal disease or to a common APOL1).

The invention also features chimeric and humanized antibodies that bind an APOL1 polypeptide (e.g., a common APOL1 or pathogenic APOL1). Chimeric antibodies preferably have constant regions derived substantially or exclusively from human antibody constant regions and variable regions derived substantially or exclusively from the sequence of the variable region from a mammal other than a human. Methods for humanizing non-human antibodies are well known in the art (for reviews see Vaswani and Hamilton, Ann. Allergy Asthma Immunol., 81:105-119, 1998 and Carter, Nature Reviews Cancer, 1:118-129, 2001). Generally, a humanized antibody has one or more amino acid residues introduced into it from a source that is non-human. These non-human amino acid residues are often referred to as import residues, which are typically taken from an import variable domain. Humanization can be essentially performed following the methods known in the art (Jones et al., Nature, 321:522-525, 1986; Riechmann et al., Nature, 332:323-329, 1988; and Verhoeyen et al., Science, 239:1534-1536 1988), by substituting rodent CDRs or other CDR sequences for the corresponding sequences of a human antibody. Accordingly, such humanized antibodies are chimeric antibodies wherein substantially less than an intact human variable domain has been substituted by the corresponding sequence from a non-human species (see for example, U.S. Pat. No. 4,816,567). In practice, humanized antibodies are typically human antibodies in which some CDR residues and possibly some FR residues are substituted by residues from analogous sites in rodent antibodies (Presta, Curr. Op. Struct. Biol. 2:593-596, 1992).

Additional methods for the preparation of humanized antibodies can be found in U.S. Pat. Nos. 5,821,337, and 6,054,297, and Carter, (supra) which are all incorporated herein by reference. The humanized antibody is selected from any class of immunoglobulins, including IgM, IgG, IgD, IgA and IgE, and any isotype, including $IgG_1$, $IgG_2$, $IgG_3$, and $IgG_4$. Where cytotoxic activity is not needed, such as in the present invention, the constant domain is preferably of the $IgG_2$ class. The humanized antibody may comprise sequences from more than one class or isotype, and selecting particular constant domains to optimize desired effector functions is within the ordinary skill in the art.

The invention also includes antibody functional derivatives that have anti-APOL1 neutralizing activity. Functional derivatives have antigen binding characteristics comparable to those of a whole antibody, and include, for example, chimeric, humanized, fully human, and single chain antibodies (e.g., scFv) or antibody fragments, antigen-binding antibody fragments, diabodies, aptamers, and antibodies fused to a second protein, or otherwise derivatized, as is known in the art. Methods of producing such functional derivatives are disclosed, for example, in PCT Publication No. WO93/21319; European Patent No. 0 239 400 B1; PCT Publication No. WO89/09622; European Patent Application No. 0338,745; European Patent Application No. 0332424; U.S. Pat. No. 4,816,567; Morrison et al., Proc. Natl. Acad. Sci. USA, 81:6851-6855, 1984; Boulianne et al., Nature, 312:643-646, 1984; Neuberger et al., Nature, 314:268-270, 1985, Smith et al., FASEB J. 19:331-341 (2005); and U.S Patent Application Publication Nos. 20050208043 and 20050276802, each of which is hereby incorporated by reference. The invention, in addition to featuring Fabs and other antibody fragments, also features methods of producing Fabs and other antibody fragments using, e.g., plasmids and host cells.

Single-chain antibody fragments (scFvs) are recombinant polypeptides which typically bind antigens or receptors; these fragments contain at least one fragment of an antibody variable heavy-chain amino acid sequence ($V_H$) tethered to at least one fragment of an antibody variable light-chain sequence ($V_L$) with or without one or more interconnecting linkers. Such a linker may be a short, flexible peptide selected to assure that the proper three-dimensional folding of the $V_L$ and $V_H$ domains occurs once they are linked so as to maintain the target molecule binding-specificity of the whole antibody from which the single-chain antibody fragment is derived. Generally, the carboxyl terminus of the $V_L$ or $V_H$ sequence is covalently linked by such a peptide linker to the amino acid terminus of a complementary $V_L$ and $V_H$ sequence. Single-chain antibody fragments can be generated by molecular cloning, antibody phage display library or similar techniques. These proteins can be produced either in eukaryotic cells or prokaryotic cells, including bacteria.

Single-chain antibody fragments contain amino acid sequences having at least one of the variable regions or CDRs of the whole antibodies described in this specification but are lacking some or all of the constant domains of those antibodies. These constant domains are not necessary for antigen binding but constitute a major portion of the structure of whole antibodies. Single-chain antibody fragments may therefore overcome some of the problems associated with the use of antibodies containing part or all of a constant domain. For example, single-chain antibody fragments tend to be free of undesired interactions between biological molecules and the heavy-chain constant region, or other unwanted biological activity. Additionally, single-chain antibody fragments are considerably smaller than whole antibodies and may therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely than whole antibodies to provoke an immune response in a recipient.

"Functional derivatives" further include fragments of antibodies that have the same or comparable binding characteristics to those of the whole antibody. Such fragments may contain one or both Fab fragments or the $F(ab')_2$ fragment (e.g., Fv, Fab, Fab', $F(ab')_2$ or other antigen-binding subsequences of antibodies). Preferably the antibody fragments contain all six CDRs of the whole antibody, although fragments containing fewer than all of such regions, such as three, four or five CDRs, may also be functional.

Derivatives of antibodies are prepared by methods known in the art. For example, fragments of antibodies may be prepared enzymatically from whole antibodies. Preferably, equivalents of antibodies are prepared from DNA encoding such equivalents. DNA encoding fragments of antibodies may be prepared by deleting all but the desired portion of the DNA that encodes the full-length antibody.

DNA encoding chimeric antibodies may be prepared by recombining DNA substantially or exclusively encoding human constant regions and DNA encoding variable regions derived substantially or exclusively from the sequence of the variable region of a mammal other than a human. DNA encoding humanized antibodies may be prepared by recombining DNA encoding constant regions and variable regions other than the CDRs derived substantially or exclusively from the corresponding human antibody regions and DNA encoding CDRs derived substantially or exclusively from a mammal other than a human.

Suitable sources of DNA molecules that encode fragments of antibodies include cells, such as hybridomas, that express the full-length antibody. The fragments may be used by themselves as antibody derivatives, or may be recombined into derivatives, as described above.

Many of the antibodies, or fragments thereof, described herein can undergo non-critical amino-acid substitutions, additions or deletions in both the variable and constant regions without loss of binding specificity or effector functions, or intolerable reduction of binding affinity (e.g., below about $10^{-7}$ M). Usually, an antibody or antibody fragment incorporating such alterations exhibits substantial sequence identity to a reference antibody or antibody fragment from which it is derived. Occasionally, a mutated antibody or antibody fragment can be selected having the same specificity and increased affinity compared with a reference antibody or antibody fragment from which it was derived. Phage-display technology offers powerful techniques for selecting such antibodies. See, e.g., Dower et al., WO 91/17271 McCafferty et al., WO 92/01047; and Huse, WO 92/06204, hereby incorporated by reference.

To screen for antibodies which bind to a particular epitope on the antigen of interest, a routine cross-blocking assay such as that described in Antibodies, A Laboratory Manual, Cold Spring Harbor Laboratory, Ed Harlow and David Lane (1988), can be performed. Alternatively, epitope mapping, e.g. as described in Champe et al., J. Biol. Chem. 270:1388-1394 (1995), can be performed to determine whether the antibody binds an epitope of interest (e.g., an epitope that includes the G1 mutation (S342G), an epitope that includes the G2 mutation (I384M), an epitope of APOL1 that lacks amino acids N388 and Y389 (i.e., the del6 mutation, which removes amino acids N388 and Y389 of APOL1), or an epitope that includes the G3 mutation (e.g., the epitope results upon expression of an APOL4/APOL1 hybrid gene due to inversion of a segment of DNA including the 5' end of APOL4, all of APOL2, and the 5' end of APOL1).

Therapeutic Protein Antagonists of APOL1

T. brucei rhodesiense can infect most humans because it produces SRA ("serum resistance-associated"; SEQ ID NO: 3), a factor that binds and neutralizes common APOL1, but not APOL1 high risk variants. Analysis of the APOL1/SRA interaction site suggests that intact SRA or its N-terminal APOL1 binding domain can be re-engineered to bind high risk APOL1 variants (e.g., pathogenic APOL1) but not common APOL1. This engineered mutant SRA could neutralize variant ApoL1 toxicity without eliminating HDL3 complexes.

For example, the SRA polypeptide could be mutated at one or more of amino acids 31-79, I58, L61, and/or I62 within its N-terminal α-helix to create a polypeptide that interacts with a pathogenic APOL1 but not a common APOL1. In a preferred embodiment, the SRA APOL1 antagonist of the invention has a sequence having at least 80% (or at least 85%, 90%, 95%, 97%, or 99% or more) sequence identity to the sequence of SEQ ID NO: 3. In other embodiments, the SRA APOL1 antagonist of the invention has a sequence having at least 80% (or at least 85%, 90%, 95%, 97%, or 99% or more) sequence identity to the sequence of amino acids 1-100; amino acids 10-90; amino acids 20-80; or amino acids 20-70 (all of SEQ ID NO: 3).

Conjugation to Therapeutic Agents or Detectable Labels

An agent of the invention (e.g., an APOL1 polypeptide or fragment thereof, an anti-APOL1 antibody or fragment thereof, or an APOL1 protein antagonist (e.g., an SRA polypeptide)) can also be coupled to a therapeutic or radioactive agent to form an agent that can be used for detection or therapeutic applications.

Radioactive agents that can be used include but are not limited to Fibrinogen $^{125}$I; Fludeoxyglucose $^{18}$F; Fluorodopa $^{18}$F; Insulin $^{125}$I; Insulin $^{131}$I; Iobenguane $^{123}$I; Iodipamide Sodium $^{131}$I; Iodoantipyrine $^{131}$I; Iodocholesterol $^{131}$I; Iodohippurate Sodium $^{123}$I; Iodohippurate Sodium $^{125}$I; Iodohippurate Sodium $^{131}$I; Iodopyracet $^{125}$I; Iodopyracet $^{131}$I; Iofetamine Hydrochloride $^{123}$I; Iomethin $^{125}$I; Iomethin $^{131}$I; Iothalamate Sodium $^{125}$I; Iothalamate Sodium $^{131}$ I; tyrosine $^{131}$I; Liothyronine $^{125}$I; Liothyronine $^{131}$I; Merisoprol Acetate $^{197}$Hg; Merisoprol Acetate $^{203}$Hg; Merisoprol $^{197}$Hg; Selenomethionine $^{75}$Se; Technetium $^{99m}$Tc Antimony Trisulfide Colloid; Technetium $^{99m}$Tc Bicisate; Technetium $^{99m}$Tc Disofenin; Technetium $^{99m}$Tc Etidronate; Technetium $^{99m}$Tc Exametazime; Technetium $^{99m}$Tc Furifosmin; Technetium $^{99m}$Tc Gluceptate; Technetium $^{99m}$Tc Lidofenin; Technetium $^{99m}$Tc Mebrofenin; Technetium $^{99m}$Tc Medronate; Technetium $^{99m}$Tc Medronate Disodium; Technetium $^{99m}$Tc Mertiatide; Technetium $^{99m}$Tc Oxidronate; Technetium $^{99m}$Tc Pentetate; Technetium $^{99m}$Tc Pentetate Calcium Trisodium; Technetium $^{99m}$Tc Sestamibi; Technetium $^{99m}$Tc Siboroxime; Technetium $^{99m}$Tc; Succimer; Technetium $^{99m}$Tc Sulfur Colloid; Technetium $^{99m}$Tc Teboroxime; Technetium $^{99m}$Tc Tetrofosmin; Technetium $^{99m}$Tc Tiatide; Thyroxine $^{125}$I: Thyroxine $^{131}$I; Tolpovidone $^{131}$I; Triolein $^{125}$I; or Triolein $^{131}$I. In preferred embodiments, the radioisotopes include, e.g., $^{123}I$, $^{124}I$, $^{125}I$, $^{131}I$, $^{99m}Tc$, $^{111}In$, $^{64}Cu$, $^{67}Cu$, $^{186}Re$, $^{188}Re$, $^{177}Lu$, $^{90}Y$, $^{77}As$, $^{72}As$, $^{86}Y$, $^{89}Zr$, $^{211}At$, $^{212}Bi$, $^{213}Bi$, and $^{225}Ac$.

The agents of the invention may also be conjugated to other, not necessarily therapeutic, moieties for the purpose of enhancing, e.g., stability or localization. Techniques for conjugating therapeutic agents to proteins, and in particular to antibodies, are well-known (e.g., Amon et al., "Monoclonal Antibodies For Immunotargeting Of Drugs In Cancer Therapy," in Monoclonal Antibodies And Cancer Therapy (Reisfeld et al., eds., Alan R. Liss, Inc., 1985); Hellstrom et al., "Antibodies For Drug Delivery," in Controlled Drug Delivery (Robinson et al., eds., Marcel Dekker, Inc., 2nd ed. 1987); Thorpe, "Antibody Carriers Of Cytotoxic Agents In Cancer Therapy: A Review," in Monoclonal Antibodies '84: Biological And Clinical Applications (Pinchera et al., eds., 1985); "Analysis, Results, and Future Prospective of the Therapeutic Use of Radiolabeled Antibody In Cancer Therapy," in Monoclonal Antibodies For Cancer Detection And Therapy (Baldwin et al., eds., Academic Press, 1985); Thorpe et al., Immunol. Rev. 62:119-58 (1982); and Doronina et al., "Development of potent monoclonal antibody auristatin conjugates for cancer therapy," Nature Biotech. 21:(7)778-784 (2003)). See also, e.g., PCT publication WO 89/12624.

Therapeutic Methods of the Invention

The invention also features methods of treating a subject having or at risk of developing a renal disease. One or more of the compositions of the invention (e.g., an APOL1 polypeptide or fragment thereof, a nucleic acid molecule encoding an APOL1 polypeptide or fragment thereof, an anti-APOL1 antibody or fragment thereof, a nucleic acid molecule encoding an anti-APOL1 antibody or fragment thereof, an anti-APOL1 nucleic acid molecule, or an APOL1 protein antagonist (e.g., an SRA polypeptide)) can be administered to treat or prevent renal disease, or to ameliorate or reduce one or more symptoms of renal disease, in patients in need thereof (e.g., patients having one or more APOL1 risk alleles).

One or more of the compositions of the invention (e.g., an APOL1 polypeptide or fragment thereof, a nucleic acid molecule encoding an APOL1 polypeptide or fragment thereof, an anti-APOL1 antibody or fragment thereof, a nucleic acid molecule encoding an anti-APOL1 antibody or fragment thereof, an anti-APOL1 nucleic acid molecule, or an APOL1 protein antagonist (e.g., an SRA polypeptide)) can also be administered to a subject in need of kidney transplantation (e.g., prior to or after transplantation). In a preferred embodiment, the subject is one that has been found to have at least one APOL1 gene risk allele (e.g., a G1, G2, G3, or del6 mutation). It is known that individuals of African ancestry, including those individuals of Hispanic ancestry and, in particular, African-Americans, have an elevated risk for carrying one or two copies of at least one risk allele the APOL1 gene, which increases their risk of developing idiopathic kidney disease. Thus, in one embodiment, a kidney recipient can be genotyped to determine if the recipient carries one or two copies of at least one of the disclosed risk alleles the APOL1 gene and can be treated prior to or after kidney transplantation with one or more of the compositions of the invention. Additionally, a kidney selected for transplantation can be treated with one or more of the compositions of the invention prior to transplantation of the kidney into the recipient.

In an embodiment, the method includes administering a therapeutically effective amount of a recombinant APOL1 protein or a fragment thereof, a recombinant anti-APOL1 antibody or fragment thereof, or an APOL1 antagonist protein (e.g., a mutated SRA polypeptide) or a delivery vehicle that includes a nucleic acid molecule encoding one or more of these polypeptides or that includes a nucleic acid molecule that inhibits expression of APOL1. In some examples, a therapeutically effective amount of recombinant APOL1 protein includes about 0.1 mg/kg to about 1000 mg/kg (such as about 1 mg/kg to 1000 mg/kg, about 10 mg/kg to 500 mg/kg, about 10 mg/kg to 100 mg/kg, about 50 mg/kg to 500 mg/kg, or about 100 mg/kg to 1000 mg/kg). Administration can be accomplished by single or multiple doses. The dose required will vary from subject to subject depending on the species, age, weight and general condition of the subject, the particular therapeutic agent being used and its mode of administration. It will be appreciated that these dosages are examples only, and an appropriate dose can be determined by one of ordinary skill in the art using only routine experimentation.

The preparation of recombinant proteins is well known to those skilled in the art. See, e.g., Sambrook et al. (In Molecular Cloning: A Laboratory Manual, CSHL, New York, 1989); Ausubel et al. (In Current Protocols in Molecular Biology, John Wiley & Sons, New York, 1998); and The Recombinant Protein Handbook, GE Lifesciences, Code 18-1142-75.

Treatment During Apheresis

The invention also features methods of treating a subject (e.g., a subject having or at risk of developing a renal disease) by contacting the blood of the subject during extracorporeal apheresis methods with one or more of the compositions of the invention (e.g., an APOL1 polypeptide or fragment thereof, an anti-APOL1 antibody or fragment thereof, or an APOL1 protein antagonist (e.g., an SRA polypeptide that binds pathogenic APOL1 but does not substantially bind (or binds at a substantially lower affinity to) common APOL1)).

Generally, apheresis includes the removal or withdrawal of blood from the subject's body, removal of one or more components from the blood, and transfusion of the remaining blood back into the subject's body. In the present invention, one or more compositions of the invention are contacted to the blood of a subject during apheresis.

Apheresis procedures and equipment are known in the art and can be used in the present invention. In one example, once the patient's blood is removed from a vein in the arm, the plasma is separated from the rest of the blood using a membrane plasma filter. Either the plasma or the blood can be contacted with one or more of the compositions of the invention and then recombined and returned to the patient.

In yet another example, blood from the patient is circulated extra-corporeally using standard apheresis equipment. The blood is separated into the cellular elements (red blood cells, white blood cells and platelets) and fluid (plasma) elements using differential centrifugation or a membrane filter. The plasma is then pumped through the targeted apheresis device where it can be contacted with one or more of the compositions of the invention. Alternatively, the other blood components can be contacted with one or more of the compositions of the invention. After the contacting step, the plasma is then mixed with the cellular blood elements and returned to the patient. In one embodiment, the pH of the blood is restored to normal biological levels prior to returning to the subject.

Additional Therapies

The agents of the invention (e.g., an APOL1 polypeptide or fragment thereof, a nucleic acid molecule encoding an APOL1 polypeptide or fragment thereof, an anti-APOL1 antibody or fragment thereof, a nucleic acid molecule encoding an anti-APOL1 antibody or fragment thereof, an anti-APOL1 nucleic acid molecule, or an APOL1 protein antagonist (e.g., an SRA polypeptide that binds pathogenic APOL1 but does not substantially bind (or binds at a substantially lower affinity to) common APOL1)) may be administered alone or in combination with other known therapies for the treatment of renal disease. For example, a subject may also be treated a blood pressure medication, a steroid, and/or an immunosuppressive agent. Examples of therapeutics include blood pressure medications (e.g., a diuretic (e.g., chlorthalidone, chlorothiazide, furosemide, hydrochlorothiazide, indapamide, metolazone, amiloride hydrochloride, spironolactone, triamterene, bumetanide, or a combination thereof), an alpha adrenergic antagonist (e.g., alfuzosin, doxazosin, prazosin, terazosin, or tamsulosin, or a combination thereof), a central adrenergic inhibitor (e.g., clonidine, guanfacine, or methyldopa, or a combination thereof), an angiotensin converting enzyme (ACE) inhibitor (e.g., benazepril, captopril, enalapril, fosinopril, lisinopril, moexipril, perindopril, quinapril, ramipril, or trandolapril, or combinations thereof), an angiotensin II receptor blocker (e.g., candesartan, eprosartan, irbesartan, losartan, olmesartan, telmisartan, or valsartan, or combinations thereof), an alpha blocker (e.g., doxazosin, prazosin, or terazosin, or a combination thereof), a beta blocker (e.g., acebutolol, atenolol, betaxolol, bisoprolol, carteolol, metoprolol, nadolol, nebivolol, penbutolol, pindolol, propranolol, solotol, or timolol, or a combination thereof), a calcium channel blocker (e.g., amlodipine, bepridil, diltiazem, felodipine, isradipine, nicardipine, nifedipine, nisoldipine, or verapamil, or combination thereof), a vasodilator (e.g., hydralazine or minoxidil, or combination thereof), and a renin inhibitor (e.g., aliskiren), or combinations thereof), a steroid (e.g., a corticosteroid, such as cortisone, prednisone, methylprednisolone, or prednisolone), or an anabolic steroid (anatrofin, anaxvar, annadrol, bolasterone, decadiabolin, decadurabolin, dehydropiandrosterone (DHEA), delatestryl, dianiabol, dihydrolone, durabolin, dymethazine, enoltestovis, equipose, gamma hydroxybutyrate, maxibolin, methatriol, methyltestosterone, parabolin, primobolin, quinolone, therabolin, trophobolene, and winstrol), or an immunosuppressive agent, such as a glucocorticoid, a cytostatic, an antibody, or an anti-immunophilin and/or mychophenolate mofetil (MMF), FK-506, azathioprine, cyclophosphamide, methotrexate, dactinomycin, antithymocyte globulin (ATGAM), an anti-CD20-antibody, a muromonoab-CD3 antibody, basilizimab, daclizumab, cyclosporin, tacrolimus, voclosporin, sirolimus, an interferon, infliximab, etanercept, adalimumab, fingolimod, and/or myriocin).

Administration and Dosage

Pharmaceutical formulations of a therapeutically effective amount of an agent of the invention (e.g., an APOL1 polypeptide or fragment thereof, a nucleic acid molecule encoding an APOL1 polypeptide or fragment thereof, an anti-APOL1 antibody or fragment thereof, a nucleic acid molecule encoding an anti-APOL1 antibody or fragment thereof, an anti-APOL1 nucleic acid molecule, or an APOL1 protein antagonist (e.g., a SRA polypeptide that preferentially binds to pathogenic APOL1 relative to common APOL1), or pharmaceutically acceptable salts thereof, can be administered orally, parenterally (e.g., as an intramuscular, intraperitoneal, intravenous, intraarterial, or subcutaneous injection), by inhalation, intradermally, by optical drops, by implant, nasally, vaginally, rectally, sublingually, or topically, and may be in admixture with a pharmaceutically acceptable carrier adapted for the route of administration.

Methods well known in the art for making formulations are found, for example, in Remington's Pharmaceutical Sciences (18$^{th}$ edition), ed. A. Gennaro, 1990, Mack Publishing Company, Easton, Pa. Compositions intended for oral use may be prepared in solid or liquid forms according to any method known to the art for the manufacture of pharmaceutical compositions. The compositions may optionally contain sweetening, flavoring, coloring, perfuming, and/or preserving agents in order to provide a more palatable preparation. Solid dosage forms for oral administration include capsules, tablets, pills, powders, and granules. In such solid forms, the active agent is admixed with at least one inert pharmaceutically acceptable carrier or excipient. These may include, for example, inert diluents, such as calcium carbonate, sodium carbonate, lactose, sucrose, starch, calcium phosphate, sodium phosphate, or kaolin. Binding agents, buffering agents, and/or lubricating agents (e.g., magnesium stearate) may also be used. Tablets and pills can additionally be prepared with enteric coatings.

Liquid dosage forms for oral administration include pharmaceutically acceptable emulsions, solutions, suspensions, syrups, and soft gelatin capsules. These forms contain inert diluents commonly used in the art, such as water or an oil medium. Besides such inert diluents, compositions can also include adjuvants, such as wetting agents, emulsifying agents, and suspending agents.

Formulations for parenteral administration include sterile aqueous or non-aqueous solutions, suspensions, or emulsions. Examples of suitable vehicles include propylene glycol, polyethylene glycol, vegetable oils, gelatin, hydrogenated naphthalenes, and injectable organic esters, such as ethyl oleate. Such formulations may also contain adjuvants, such as preserving, wetting, emulsifying, and dispersing agents. Biocompatible, biodegradable lactide polymer, lactide/glycolide copolymer, or polyoxyethylene-polyoxypropylene copolymers may be used to control the release of the compounds. Other potentially useful parenteral delivery systems for the agents of the invention include ethylene-vinyl acetate copolymer particles, osmotic pumps, implantable infusion systems, and liposomes.

Liquid formulations can be sterilized by, for example, filtration through a bacteria-retaining filter, by incorporating sterilizing agents into the compositions, or by irradiating or heating the compositions. Alternatively, they can also be manufactured in the form of sterile, solid compositions, which can be dissolved in sterile water or some other sterile injectable medium immediately before use.

Compositions for rectal or vaginal administration are preferably suppositories, which may contain, in addition to active substances, excipients such as cocoa butter or a suppository wax. Compositions for nasal or sublingual administration are also prepared with standard excipients known in the art. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops or spray, or as a gel.

The amount of active ingredient (e.g., an APOL1 polypeptide or fragment thereof, a nucleic acid molecule encoding an APOL1 polypeptide or fragment thereof, an anti-APOL1 antibody or fragment thereof, a nucleic acid molecule encoding an anti-APOL1 antibody or fragment thereof, an anti-APOL1 nucleic acid molecule, or an APOL1 protein antagonist (e.g., a SRA polypeptide that preferentially binds to pathogenic APOL1 relative to common APOL1)) in the compositions of the invention can be varied.

One skilled in the art will appreciate that the exact individual dosages may be adjusted somewhat depending upon a variety of factors, including the ingredient being administered, the time of administration, the route of administration, the nature of the formulation, the rate of excretion, the nature of the subject's conditions, and the age, weight, health, and gender of the patient. In addition, the severity of the condition targeted by an agent of the invention will also have an impact on the dosage level. Generally, dosage levels of an agent of the invention of between 0.1 μg/kg to 100 mg/kg of body weight are administered daily, weekly, monthly, or yearly as a single dose or divided into multiple doses (e.g., 2-12 doses per day, week, month, or year), or as needed. Preferably, the general dosage range is between 250 μg/kg to 50.0 mg/kg of body weight per day. Wide variations in the needed dosage are to be expected in view of the differing efficiencies of the various routes of administration. For instance, oral administration generally would be expected to require higher dosage levels than administration by intravenous injection. Variations in these dosage levels can be adjusted using standard empirical routines for optimization, which are well known in the art. In general, the precise therapeutically effective dosage will be determined by the attending physician in consideration of the above-identified factors.

An agent of the (e.g., an APOL1 polypeptide or fragment thereof, a nucleic acid molecule encoding an APOL1 polypeptide or fragment thereof, an anti-APOL1 antibody or fragment thereof, a nucleic acid molecule encoding an anti-APOL1 antibody or fragment thereof, an anti-APOL1 nucleic acid molecule, or an APOL1 protein antagonist (e.g., a SRA polypeptide that preferentially binds to pathogenic APOL1 relative to common APOL1))) can be administered in a sustained release composition, such as those described in, for example, U.S. Pat. Nos. 5,672,659 and 5,595,760, hereby incorporated by reference, or as a liposomal formulation. The use of immediate or sustained release compositions depends on the type of condition being treated. If the condition consists of an acute or over-acute disorder, a treatment with an immediate release form will be preferred over a prolonged release composition. Alternatively, for preventative or long-term treatments, a sustained released composition will generally be preferred.

Where sustained release administration of the agent (e.g., an antibody, peptide, or nucleic acid molecule) is desired in a formulation with release characteristics suitable for the treatment of any disease or disorder requiring administration of the agent (e.g., treatment of renal disease), microencapsulation of the agent is contemplated. Microencapsulation of recombinant proteins for sustained release has been successfully performed with human growth hormone (rhGH), interferon-(rhIFN-), interleukin-2, and MN rgp120 (Johnson et al., Nat. Med. 2: 795-799, 1996; Yasuda, Biomed. Ther. 27: 1221-1223, 1993; Hora et al., Bio/Technology 8: 755-758 1990; Cleland, "Design and Production of Single Immunization Vaccines Using Polylactide Polyglycolide Microsphere Systems," in "Vaccine Design: The Subunit and Adjuvant Approach," Powell and Newman, Eds., Plenum Press: New York, pp. 439-462, 1995; WO 97/03692; WO 96/40072; WO 96/07399; and U.S. Pat. No. 5,654,010, hereby incorporated by reference).

The sustained-release formulations may also include those developed using poly-lactic-coglycolic acid (PLGA) polymer. The degradation products of PLGA, lactic and glycolic acids, can be cleared quickly from the human body. Moreover, the degradability of this polymer can be adjusted from months to years depending on its molecular weight and composition (see, e.g., Lewis, "Controlled release of bioactive agents from lactide/glycolide polymer," in M. Chasin and Dr. Langer (Eds.), Biodegradable Polymers as Drug Delivery Systems (Marcel Dekker: New York, pp. 1-41, 1990)).

An agent of the invention (e.g., an APOL1 polypeptide or fragment thereof, a nucleic acid molecule encoding an APOL1 polypeptide or fragment thereof, an anti-APOL1 antibody or fragment thereof, a nucleic acid molecule encoding an anti-APOL1 antibody or fragment thereof, an anti-APOL1 nucleic acid molecule, or an APOL1 protein antagonist (e.g., a SRA polypeptide that preferentially binds to pathogenic APOL1 relative to common APOL1)) can be prepared in any suitable manner. The agent may be isolated from naturally-occurring sources, recombinantly produced, or produced synthetically, identified from a library, or produced by a combination of these methods. The synthesis of short peptides, e.g., is well known in the art. As described previously, a peptide portion of any of the agents of the invention can be synthesized according to standard peptide synthesis methods known in the art.

Methods for administering peptides to a subject are described, for example, in U.S. Pat. Nos. 5,830,851; 5,558,085; 5,916,582; 5,960,792; and 6,720,407, hereby incorporated by reference.

Assessment of Therapy

After therapeutic treatment with the compositions of the invention described herein, the efficacy of the treatment may be assessed by a number of methods, such as assays that measure hypoalbuminemia (low serum albumin) in the blood, a reduction in symptoms of hyperlipidemia and hypertension (high blood pressure), a reduction in edema (fluid retention), a reduction in inflammation in the kidney (e.g., in the nephron), a reduction in protein in the urine (proteinuria), a reduction of blood in the uring (hematuria), and/or an increase in renal function. Tests that can be performed include urinalysis, blood tests (for, e.g., cholesterol), and kidney biopsy (e.g., a reduction in sclerosis (scarring) of the glomerulus). Efficacy may also be indicated by an improvement in or resolution of one or more symptoms of renal disease or in a reduced need of, or frequency of, dialysis.

Diagnostics

A patient that may be in need of one or more of the treatment methods and compositions described herein can be identified by detecting one or more APOL1 risk alleles in the patient (e.g., one or more of the G1, G3, del6, or G3 risk alleles described herein). Preferably, the patient includes two or more APOL1 risk alleles. In other embodiments, the subject is of African or Hispanic ancestry. For example, subjects of African or Hispanic ancestry that have at least two (or more) of APOL1 gene risk alleles exhibit a significantly increased risk of developing renal disease. Thus, these subjects may be assayed for the presence of a wild type allele (relative to an APOL1 gene risk allele) as a means for determining whether the subject has a moderate or increased risk of renal disease. For example, a subject that is heterozygous at a given locus for one or more of the APOL1 gene risk alleles may have a greater risk of renal disease relative to a subject lacking any APOL1 gene risk alleles, and thus may be more likely to benefit from treatment using one or more of the methods or compositions described herein. A subject that is homozygous at a given locus for one or more APOL1 gene risk alleles may have a greater risk of renal disease, relative to a subject that is heterozygous for an APOL1 gene risk allele at that locus or a subject that lacks any risk alleles in an APOL1 gene, and thus may be more likely to benefit from treatment using one or more of the methods or compositions described herein. The presence of two or more (e.g., three, four, or more) risk alleles at different loci further increases the likelihood of renal disease in a subject. Thus a subject having two or more (e.g., three, four, or more) risk alleles at different loci is likely to benefit from treatment using one or more of the methods or compositions described herein.

Thus, the present invention also features a method of diagnosing a subject that is likely to benefit from one or more of the treatment methods and compositions described herein by using one or more of the methods or kits described in, e.g., PCT/US2011/032924, which is incorporated herein by reference, to identify the present or absence of one or more APOL1 risk alleles in the subject. Once the subject has been identified as having one or more (or two, three, or four, or more) APOL1 risk alleles at one or more loci, and thus to have or to be at a greater risk of developing a renal disease, the subject may be administered one or more of the compositions of the invention in order to treat (prophylactically or therapeutically) the renal disease or to reduce one or more of the symptoms of the renal disease.

The invention also provides for a diagnostic test kit for detecting the presence of one or more APOL1 risk alleles. The invention also provides a kit for treating a subject once a diagnosis that the subject has or is at risk of developing renal disease has been made. The kit may include the diagnostic reagents and instructions for detecting the presence of an APOL1 risk allele only or the diagnostic reagents and one or more compositions for treating the renal disease (e.g., an APOL1 polypeptide or fragment thereof, a nucleic acid molecule encoding an APOL1 polypeptide or fragment thereof, an anti-APOL1 antibody or fragment thereof, or a nucleic acid molecule encoding an anti-APOL1 antibody or fragment thereof) and, optionally, instructions for performing the diagnosis and the treatment methods, or only compositions for treating the renal disease and, optionally, instructions for the treatment methods. The kit may also include one or more other therapeutic agents, such as a blood pressure medication, a steroid, or an antinflammatory agent.

EXAMPLES

In order to make the compositions of the present invention and methods of their use clearer, the following examples are presented. These examples are only for illustrative purposes and should not be interpreted in any way as limitations on the compositions and uses of this invention.

Example 1

Biotherapeutic Readout in Clinic: Preclinical Read-Outs of Neutralization or Antagonism Efficacy and physiological folding of common APOL1 can be tested by its ability to pull down recombinant SRA, the natural ligand expressed by T. brucei rhodesiense that confers human infectivity by binding ApoL1.

Preferably, an antibody of the invention is raised against an epitope in the SRA-binding region (amino acids 339-389 of SEQ ID NO: 2) that encompasses disease associated variant sequences (e.g., G1, G2, del6, and/or G3).

Preferred recombinant APOL1 proteins of the invention will bind to haptoglobin-related protein (HPR) and to the HPR-hemoglobin (Hb) complex (Vanhollebeke et al., Proceedings of the National Academy of Sciences of the United States of America 104:4118-4123, 2007).

The efficacy of monoclonal anti-APOL1 antibodies can be tested by standard techniques of ELISA, immunoblot, immunoprecipitation, immunohistochemistry, and immunofluorescence microscopy.

Immunoprecipitation-competent antibodies can be tested for pull-down of APOL1 in complex with HPR, in complex with HPR-Hb, and within native HDL3.

Mutant SRA polypeptides of the invention can be tested for their ability to selectively bind high risk APOL1 variants (pathogenic APOL1) but not common APOL1, using pull-down assays, surface plasmon resonance assays, and isothermal titration calorimetry.

Example 2

Biotherapeutic Readout in Clinic: In-Human Readout

In humans with two high risk APOL1 alleles, pharmacokinetics and stability of recombinant common APOL1 in the circulation can be confirmed by immunoreactivity to antibody that recognizes only common variant Apo-L1, but not Apo-L1 high risk variants.

In humans, recombinant SRA APOL1 binding domain can be measured by immunoassay.

Therapeutic efficacy upon administration of one or more of the compositions of the invention can be assessed by measuring changes (e.g., a decrease) in, e.g., proteinuria, which is a cardinal feature of renal disease and is easily measured, and/or changes in serum creatinine concentration.

Example 3

Treatment of Renal Disease Patients that are Refractive to Other Therapies

African American patients with FSGS that do not respond to steroid treatment can be genotyped for APOL1 renal risk variants. Homozygous patients can be treated with one or more compositions of the invention described above (alone or in combination with one or more other therapeutic agents, such as a blood pressure medication, a steroid, and/or an immunosuppressive agent). Clinical readouts include urine protein and serum creatinine concentration levels. Since patients would have already failed first line therapy, differentiation from other therapies would be achievable.

OTHER EMBODIMENTS

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described herein. The term "comprises" means "includes." In case of conflict, the present specification, including explanations of terms, will control. In addition, the materials, methods, and examples are illustrative only and not intended to be limiting.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All publications and patent applications mentioned in this specification are herein incorporated by reference to the same extent as if each independent publication or patent application was specifically and individually indicated to be incorporated by reference in their entirety.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

An exemplary nucleic acid sequence for human apolipoprotein L1 is:

(SEQ ID NO: 1)

```
atggagggag ctgctttgct gagagtctct gtcctctgca tctggatgag tgcacttttc

cttggtgtgg gagtgagggc agaggaagct ggagcgaggg tgcaacaaaa cgttccaagt

gggacagata ctggagatcc tcaaagtaag cccctcggtg actgggctgc tggcaccatg

gacccagaga gcagtatctt tattgaggat gccattaagt atttcaagga aaaagtgagc

acacagaatc tgctactcct gctgactgat aatgaggcct ggaacggatt cgtggctgct

gctgaactgc ccaggaatga ggcagatgag ctccgtaaag ctctggacaa ccttgcaaga

caaatgatca tgaaagacaa aaactggcac gataaaggcc agcagtacag aaactggttt

ctgaaagagt ttcctcggtt gaaaagtgag cttgaggata acataagaag gctccgtgcc

cttgcagatg gggttcagaa ggtccacaaa ggcaccacca tcgccaatgt ggtgtctggc

tctctcagca tttcctctgg catcctgacc ctcgtcggca tgggtctggc acccttcaca

gagggaggca gccttgtact cttggaacct gggatggagt tgggaatcac agccgctttg

accgggatta ccagcagtac catggactac ggaaagaagt ggtggacaca agcccaagcc

cacgacctgg tcatcaaaag ccttgacaaa ttgaaggagg tgagggagtt tttgggtgag

aacatatcca actttctttc cttagctggc aatacttacc aactcacacg aggcattggg

aaggacatcc gtgccctcag acgagccaga gccaatcttc agtcagtacc gcatgcctca

gcctcacgcc cccgggtcac tgagccaatc tcagctgaaa gcggtgaaca ggtggagagg

gttaatgaac ccagcatcct ggaaatgagc agaggagtca agctcacgga tgtggcccct

gtaagcttct ttcttgtgct ggatgtagtc tacctcgtgt acgaatcaaa gcacttacat

gagggggcaa agtcagagac agctgaggag ctgaagaagg tggctcagga gctggaggag

aagctaaaca ttctcaacaa taattataag attctgcagg cggaccaaga actgtga
```

An exemplary amino acid sequence for human apolipoprotein L1 is:

(SEQ ID NO: 2)

```
MEGAALLRVS VLCIWMSALF LGVGVRAEEA GARVQQNVPS GTDTGDPQSK PLGDWAAGTM

DPESSIFIED AIKYFKEKVS TQNLLLLLTD NEAWNGFVAA AELPRNEADE LRKALDNLAR

QMIMKDKNWH DKGQQYRNWF LKEFPRLKSE LEDNIRRLRA LADGVQKVHK GTTIANVVSG

SLSISSGILT LVGMGLAPFT EGGSLVLLEP GMELGITAAL TGITSSTMDY GKKWWTQAQA

HDLVIKSLDK LKEVREFLGE NISNFLSLAG NTYQLTRGIG KDIRALRRAR ANLQSVPHAS

ASRPRVTEPI SAESGEQVER VNEPSILEMS RGVKLTDVAP VSFFLVLDVV YLVYESKHLH

EGAKSETAEE LKKVAQELEE KLNILNNNYK ILQADQEL
```

An exemplary amino acid sequence for human serum resistance associated (*Trypanosoma bruscei*) is:

(SEQ ID NO: 3)

```
TTSTLALALA LKLLAVPVSP SGTAFDEEPV KKVCKVEKNL ADVAGIALAK INNLIKQVSA

ATEAEARMTL AAASTDHSNI SALYAAASNI VTRCVLNAVH ALTSLAPIAL TAATNGAKTS

GHISEVIDIL QQASQGKTEG KCIVKSGGGT TTVAIRQLYN KIGDLEKQTT NNCGTSVTEV
```

-continued

LEHILKQEAL KEALLSIVKK PKGAPDKTAA DELVTALING VVPNSTAQTQ KLKEKILNTL

VPKLVEGSKS QVKLRILKYP GKIQKSKLVS IQELKTRVEP ESSTESCKQQ VATNQAQEAF

CNAIGDDKDK CNNETRCSYD DSKGSDKKCT YNAEKAEANG APATQPQGGV NEATTGNCKG

KLEPGCTKAQ EYEWEGKESK DSSFLVDMKL ALNMVA

---

SEQUENCE LISTING

<160> NUMBER OF SEQ ID NOS: 4

<210> SEQ ID NO 1
<211> LENGTH: 1197
<212> TYPE: DNA
<213> ORGANISM: Homo sapiens

<400> SEQUENCE: 1 atggagggag ctgctttgct gagagtctct gtcctctgca tctggatgag tgcacttttc 60 cttggtgtgg gagtgagggc agaggaagct ggagcgaggg tgcaacaaaa cgttccaagt 120 gggacagata ctggagatcc tcaaagtaag cccctcggtg actgggctgc tggcaccatg 180 gacccagaga gcagtatctt tattgaggat gccattaagt atttcaagga aaaagtgagc 240 acacagaatc tgctactcct gctgactgat aatgaggcct ggaacggatt cgtggctgct 300 gctgaactgc ccaggaatga ggcagatgag ctccgtaaag ctctggacaa ccttgcaaga 360 caaatgatca tgaaagacaa aaactggcac gataaaggcc agcagtacag aaactggttt 420 ctgaaagagt ttcctcggtt gaaaagtgag cttgaggata acataagaag gctccgtgcc 480 cttgcagatg gggttcagaa ggtccacaaa ggcaccacca tcgccaatgt ggtgtctggc 540 tctctcagca tttcctctgg catcctgacc ctcgtcggca tgggtctggc acccttcaca 600 gagggaggca gccttgtact cttggaacct gggatggagt tgggaatcac agccgctttg 660 accgggatta ccagcagtac catggactac ggaaagaagt ggtggacaca agcccaagcc 720 cacgacctgg tcatcaaaag ccttgacaaa ttgaaggagg tgagggagtt tttgggtgag 780 aacatatcca actttctttc cttagctggc aatacttacc aactcacacg aggcattggg 840 aaggacatcc gtgccctcag acgagccaga gccaatcttc agtcagtacc gcatgcctca 900 gcctcacgcc cccgggtcac tgagccaatc tcagctgaaa gcggtgaaca ggtggagagg 960 gttaatgaac ccagcatcct ggaaatgagc agaggagtca agctcacgga tgtggcccct 1020 gtaagcttct ttcttgtgct ggatgtagtc tacctcgtgt acgaatcaaa gcacttacat 1080 gagggggcaa agtcagagac agctgaggag ctgaagaagg tggctcagga gctggaggag 1140 aagctaaaca ttctcaacaa taattataag attctgcagg cggaccaaga actgtga 1197

<210> SEQ ID NO 2
<211> LENGTH: 398
<212> TYPE: PRT
<213> ORGANISM: Homo sapiens

<400> SEQUENCE: 2

Met Glu Gly Ala Ala Leu Leu Arg Val Ser Val Leu Cys Ile Trp Met
1 5 10 15

Ser Ala Leu Phe Leu Gly Val Gly Val Arg Ala Glu Glu Ala Gly Ala
20 25 30

Arg Val Gln Gln Asn Val Pro Ser Gly Thr Asp Thr Gly Asp Pro Gln
35 40 45

```
Ser Lys Pro Leu Gly Asp Trp Ala Ala Gly Thr Met Asp Pro Glu Ser
    50                  55                  60

Ser Ile Phe Ile Glu Asp Ala Ile Lys Tyr Phe Lys Glu Lys Val Ser
65                  70                  75                  80

Thr Gln Asn Leu Leu Leu Leu Leu Thr Asp Asn Glu Ala Trp Asn Gly
                85                  90                  95

Phe Val Ala Ala Ala Glu Leu Pro Arg Asn Glu Ala Asp Glu Leu Arg
            100                 105                 110

Lys Ala Leu Asp Asn Leu Ala Arg Gln Met Ile Met Lys Asp Lys Asn
        115                 120                 125

Trp His Asp Lys Gly Gln Gln Tyr Arg Asn Trp Phe Leu Lys Glu Phe
    130                 135                 140

Pro Arg Leu Lys Ser Glu Leu Glu Asp Asn Ile Arg Arg Leu Arg Ala
145                 150                 155                 160

Leu Ala Asp Gly Val Gln Lys Val His Lys Gly Thr Thr Ile Ala Asn
                165                 170                 175

Val Val Ser Gly Ser Leu Ser Ile Ser Ser Gly Ile Leu Thr Leu Val
            180                 185                 190

Gly Met Gly Leu Ala Pro Phe Thr Glu Gly Gly Ser Leu Val Leu Leu
        195                 200                 205

Glu Pro Gly Met Glu Leu Gly Ile Thr Ala Ala Leu Thr Gly Ile Thr
    210                 215                 220

Ser Ser Thr Met Asp Tyr Gly Lys Lys Trp Trp Thr Gln Ala Gln Ala
225                 230                 235                 240

His Asp Leu Val Ile Lys Ser Leu Asp Lys Leu Lys Glu Val Arg Glu
                245                 250                 255

Phe Leu Gly Glu Asn Ile Ser Asn Phe Leu Ser Leu Ala Gly Asn Thr
            260                 265                 270

Tyr Gln Leu Thr Arg Gly Ile Gly Lys Asp Ile Arg Ala Leu Arg Arg
        275                 280                 285

Ala Arg Ala Asn Leu Gln Ser Val Pro His Ala Ser Ala Ser Arg Pro
    290                 295                 300

Arg Val Thr Glu Pro Ile Ser Ala Glu Ser Gly Glu Gln Val Glu Arg
305                 310                 315                 320

Val Asn Glu Pro Ser Ile Leu Glu Met Ser Arg Gly Val Lys Leu Thr
                325                 330                 335

Asp Val Ala Pro Val Ser Phe Phe Leu Val Leu Asp Val Val Tyr Leu
            340                 345                 350

Val Tyr Glu Ser Lys His Leu His Glu Gly Ala Lys Ser Glu Thr Ala
        355                 360                 365

Glu Glu Leu Lys Lys Val Ala Gln Glu Leu Glu Glu Lys Leu Asn Ile
    370                 375                 380

Leu Asn Asn Asn Tyr Lys Ile Leu Gln Ala Asp Gln Glu Leu
385                 390                 395


<210> SEQ ID NO 3
<211> LENGTH: 396
<212> TYPE: PRT
<213> ORGANISM: Trypanosoma brucei

<400> SEQUENCE: 3

Thr Thr Ser Thr Leu Ala Leu Ala Leu Ala Leu Lys Leu Leu Ala Val
1               5                   10                  15

Pro Val Ser Pro Ser Gly Thr Ala Phe Asp Glu Glu Pro Val Lys Lys
            20                  25                  30
```

```
Val Cys Lys Val Glu Lys Asn Leu Ala Asp Val Ala Gly Ile Ala Leu
        35                  40                  45

Ala Lys Ile Asn Asn Leu Ile Lys Gln Val Ser Ala Ala Thr Glu Ala
    50                  55                  60

Glu Ala Arg Met Thr Leu Ala Ala Ala Ser Thr Asp His Ser Asn Ile
65                  70                  75                  80

Ser Ala Leu Tyr Ala Ala Ala Ser Asn Ile Val Thr Arg Cys Val Leu
                85                  90                  95

Asn Ala Val His Ala Leu Thr Ser Leu Ala Pro Ile Ala Leu Thr Ala
            100                 105                 110

Ala Thr Asn Gly Ala Lys Thr Ser Gly His Ile Ser Glu Val Ile Asp
        115                 120                 125

Ile Leu Gln Gln Ala Ser Gln Gly Lys Thr Glu Gly Lys Cys Ile Val
    130                 135                 140

Lys Ser Gly Gly Gly Thr Thr Thr Val Ala Ile Arg Gln Leu Tyr Asn
145                 150                 155                 160

Lys Ile Gly Asp Leu Glu Lys Gln Thr Thr Asn Asn Cys Gly Thr Ser
                165                 170                 175

Val Thr Glu Val Leu Glu His Ile Leu Lys Gln Glu Ala Leu Lys Glu
            180                 185                 190

Ala Leu Leu Ser Ile Val Lys Lys Pro Lys Gly Ala Pro Asp Lys Thr
        195                 200                 205

Ala Ala Asp Glu Leu Val Thr Ala Leu Ile Asn Gly Val Val Pro Asn
    210                 215                 220

Ser Thr Ala Gln Thr Gln Lys Leu Lys Glu Lys Ile Leu Asn Thr Leu
225                 230                 235                 240

Val Pro Lys Leu Val Glu Gly Ser Lys Ser Gln Val Lys Leu Arg Ile
                245                 250                 255

Leu Lys Tyr Pro Gly Lys Ile Gln Lys Ser Lys Leu Val Ser Ile Gln
            260                 265                 270

Glu Leu Lys Thr Arg Val Glu Pro Glu Ser Ser Thr Glu Ser Cys Lys
        275                 280                 285

Gln Gln Val Ala Thr Asn Gln Ala Gln Glu Ala Phe Cys Asn Ala Ile
    290                 295                 300

Gly Asp Asp Lys Asp Lys Cys Asn Asn Glu Thr Arg Cys Ser Tyr Asp
305                 310                 315                 320

Asp Ser Lys Gly Ser Asp Lys Lys Cys Thr Tyr Asn Ala Glu Lys Ala
                325                 330                 335

Glu Ala Asn Gly Ala Pro Ala Thr Gln Pro Gln Gly Gly Val Asn Glu
            340                 345                 350

Ala Thr Thr Gly Asn Cys Lys Gly Lys Leu Glu Pro Gly Cys Thr Lys
        355                 360                 365

Ala Gln Glu Tyr Glu Trp Glu Gly Lys Glu Ser Lys Asp Ser Ser Phe
    370                 375                 380

Leu Val Asp Met Lys Leu Ala Leu Asn Met Val Ala
385                 390                 395
```

<210> SEQ ID NO 4
<211> LENGTH: 16
<212> TYPE: DNA
<213> ORGANISM: Artificial Sequence
<220> FEATURE:
<223> OTHER INFORMATION: Synthetic Construct -continued

```
<400> SEQUENCE: 4

taacgttgag gggcat                                                    16
```

What is claimed is:

[1. A method of treating or reducing the likelihood of development of a renal disease comprising administering to a human subject expressing at least one pathogenic human APOL1 polypeptide comprising an S342G substitution, an I384M substitution, or a deletion removing amino acids N388 and Y389 a composition comprising an anti-APOL1 antibody or fragment thereof that specifically binds to the pathogenic APOL1 polypeptide, but does not specifically bind, or binds at a substantially greater dissociation constant, to a non-pathogenic APOL1 polypeptide, wherein said composition decreases a deleterious effect of the pathogenic APOL1 polypeptide.]

[2. The method of claim 1, wherein said anti-APOL1 antibody or fragment thereof neutralizes said human pathogenic APOL1 polypeptide.]

[3. The method of claim 1, wherein said composition treats or substantially inhibits development of said renal disease or treats or reduces one or more symptoms associated with said renal disease.]

[4. The method of claim 1, wherein said renal disease glomerulosclerosis.]

[5. The method of claim 1 further comprising, prior to administering said inhibitor, determining the expression of at least one pathogenic APOL1 polypeptide in said subject.]

[6. The method of claim 5, wherein the subject is homozygous or heterozygous for at least one or more APOL1 alleles that encode said pathogenic APOL1 polypeptide.]

[7. The method of claim 1, wherein the subject is an African-American subject.]

[8. The method of claim 1 further comprising administering to said subject a therapeutic agent selected from the group consisting of a blood pressure medication and a cholesterol-lowering medication.]

[9. The method of claim 1, wherein said renal disease is selected from the group consisting of focal segmental glomerulosclerosis (FSGS), end-stage kidney disease (ESKD), hypertensive ESKD, idiopathic nephritic syndrome, and human immunodeficiency virus (HIV)-associated nephropathy.]

*10. A method of treating or reducing the likelihood of developing a renal disease in a subject with an apolipoprotein L1 (APOL1) genotype selected from the group consisting of:*

*i) at least one copy of the G1 allele of APOL1;*

*ii) at least one copy of the G2 allele of APOL1;*

*iii) at least one copy of the G3 allele of APOL1; and*

*iv) at least one copy of the del6 allele of APOL1;*

*wherein the G1 allele, the G2 allele, the G3 allele, and the del6 allele of APOL1 encode a pathogenic APOL1 polypeptide,*

*wherein the method comprises administering to the subject a composition comprising a nucleic acid molecule comprising at least 15 contiguous nucleotides identical or complementary to a portion of a sequence encoding said pathogenic APOL1 polypeptide.*

*11. The method of claim 10, wherein said nucleic acid molecule is a ribonucleic acid interfering (RNAi) molecule or an antisense oligonucleotide.*

*12. The method of claim 11, wherein said RNAi molecule is an siRNA, shRNA, dsRNA, or miRNA.*

*13. The method of claim 10, wherein said nucleic acid molecule is an antisense oligonucleotide.*

*14. The method of claim 10, wherein said nucleic acid molecule comprises a sequence complementary to at least 15 contiguous nucleotides set forth within nucleotides 1-1197 of SEQ ID NO: 1.*

*15. The method of claim 14, wherein said nucleic acid molecule comprises a sequence complementary to at least 15 contiguous nucleotides set forth within nucleotides 1-200 of SEQ ID NO: 1.*

*16. The method of claim 14, wherein said nucleic acid molecule comprises a sequence complementary to at least 15 contiguous nucleotides set forth within nucleotides 1014-1197 of SEQ ID NO: 1.*

*17. The method of claim 10, wherein said nucleic acid molecule comprises:*

*(a) a nucleotide sequence having at least 85% sequence identity to a nucleotide sequence complementary to at least 15 contiguous nucleotides set forth in SEQ ID NO: 1, and*

*(b) one or more mutations associated with the G1, G2, G3, or del6 allele of APOL1.*

*18. The method of claim 10 wherein said nucleic acid molecule comprises a sequence having at least 90% sequence identity to said sequence complementary to at least 15 contiguous nucleotides set forth in SEQ ID NO: 1.*

*19. The method of claim 18, wherein said nucleic acid molecule comprises a sequence having at least 95% sequence identity to said sequence complementary to at least 15 contiguous nucleotides set forth in SEQ ID NO: 1.*

*20. The method of claim 19, wherein said nucleic acid molecule comprises a sequence having at least 97% sequence identity to said sequence complementary to at least 15 contiguous nucleotides set forth in SEQ ID NO: 1.*

*21. The method of claim 20, wherein said nucleic acid molecule comprises a sequence having at least 99% sequence identity to said sequence complementary to at least 15 contiguous nucleotides set forth in SEQ ID NO: 1.*

*22. The method of claim 21, wherein said nucleic acid molecule comprises a sequence having 100% sequence identity to said sequence complementary to at least 15 contiguous nucleotides set forth in SEQ ID NO: 1.*

*23. The method of claim 14, wherein said nucleic acid molecule comprises a sequence complementary to at least 50 contiguous nucleotides set forth within nucleotides 1-1197 of SEQ ID NO: 1.*

*24. The method of claim 10, wherein said nucleic acid molecule decreases the level of expression of the pathogenic APOL1 polypeptide by at least about 20%.*

*25. The method of claim 10, wherein said composition further comprises a vector comprising said nucleic acid molecule.*

*26. The method of claim 25, wherein said vector is a viral or non-viral vector.*

*27. The method of claim 25, wherein said viral vector is an adenoviral, rhabdoviral vector, retroviral vector, adeno-associated vector, poxviral vector, herpes viral vector, or Sindbis viral vector.*

*28. The method of claim 10, wherein said composition further comprises a pharmaceutically acceptable excipient, diluent, or salt.*

*29. The method of claim 10, further comprising delivering said nucleic acid molecule into a cell of the subject, wherein said nucleic acid molecule reduces or inhibits expression of the pathogenic APOL1 polypeptide in the cell.*

*30. The method of claim 10, wherein said subject is a human.*

*31. The method of claim 30, wherein said subject is of African or Hispanic ancestry.*

*32. The method of claim 10, wherein said renal disease is selected from the group consisting of focal segmental glomerulosclerosis (FSGS), end-stage kidney disease (ESKD), hypertensive ESKD, nephropathy secondary to systemic lupus erythematosus, diabetic nephropathy, hypertensive nephropathy, IgA nephropathy, nephritis, human immunodeficiency virus (HIV)-associated nephropathy, non-diabetic chronic kidney disease, and xanthine oxidase deficiency.*

*33. The method of claim 32, wherein said renal disease is FSGS or ESKD.*

*34. The method of claim 10, wherein the nucleic acid molecule comprises a locked nucleic acid (LNA).*

*35. The method of claim 24, wherein the nucleic acid molecule decreases the level of expression of the pathogenic APOL1 polypeptide by at least 50%.*

*36. The method of claim 10, wherein the subject is homozygous for the G1 allele, G2 allele, G3 allele, and/or del6 allele of APOL1.*

*37. The method of claim 12, wherein the siRNA molecule contains 3' overhangs selected from the group consisting of:*

*i) a single uracil overhang at each 3' end of the siRNA;*

*ii) a double uracil overhang at each 3' end of the siRNA;*

*iii) a single thymine overhang at each 3' end of the siRNA; or*

*iv) a double uracil overhang at each 3' end of the siRNA.*

* * * * *